(12) United States Patent
Frazier et al.

(10) Patent No.: US 7,473,244 B2
(45) Date of Patent: Jan. 6, 2009

(54) ACTIVE NEEDLE DEVICES WITH INTEGRATED FUNCTIONALITY

(75) Inventors: A. Bruno Frazier, Mableton, GA (US); Joseph D. Andrade, Salt Lake City, UT (US); Daniel A. Bartholomeusz, Murray, UT (US); John D. Brazzle, Milford, NH (US)

(73) Assignee: The University of Utah Research Foundation, Salt Lake City, UT (US)

( * ) Notice: Subject to any disclaimer, the term of this patent is extended or adjusted under 35 U.S.C. 154(b) by 336 days.

(21) Appl. No.: 10/258,011

(22) PCT Filed: Jun. 1, 2001

(86) PCT No.: PCT/US01/17838

§ 371 (c)(1),
(2), (4) Date: Feb. 23, 2004

(87) PCT Pub. No.: WO01/93930

PCT Pub. Date: Dec. 13, 2001

(65) Prior Publication Data

US 2004/0176732 A1  Sep. 9, 2004

(51) Int. Cl.
*A61M 5/32* (2006.01)
*A61B 5/05* (2006.01)

(52) U.S. Cl. .................. 604/272; 600/385

(58) Field of Classification Search ............ 604/272, 604/890.1–892.1, 65–67; 600/345
See application file for complete search history.

(56) References Cited

U.S. PATENT DOCUMENTS

| 4,285,779 A | 8/1981 | Shiga et al. |
| 4,493,753 A | 1/1985 | Becker et al. |
| 4,530,740 A | 7/1985 | Wolf et al. |
| 4,707,225 A | 11/1987 | Schuler et al. |
| 4,780,395 A | 10/1988 | Saito et al. |
| 4,784,737 A * | 11/1988 | Ray et al. ............... 435/455 |
| 4,837,049 A | 6/1989 | Byers et al. |
| 4,871,623 A | 10/1989 | Hoopman et al. |

(Continued)

FOREIGN PATENT DOCUMENTS

WO     WO 00/16833     3/2000

OTHER PUBLICATIONS

Wood, Keith & Moika Gruber. "Transduction in microbial biosensors using multiplexed bioluminescence." Biosensors and Bioelectronics. Voll 11, No. 3: 1996 pp. 207-214.*

*Primary Examiner*—Kevin C. Sirmons
*Assistant Examiner*—Elizabeth R MacNeill
(74) *Attorney, Agent, or Firm*—Workman Nydegger

(57) ABSTRACT

An active needle device for fluid injection or extraction includes at least one hollow elongated shaft defining at least one channel. The channel provides communication between at least one input port and at least one output port of the needle device. At least one active component such as a sensor or actuator is placed or integrated into the elongated shaft. The needle device can include a macroneedle, a microneedle, or an array of macroneedles or microneedles. The microneedles can be fabricated on a substrate which can remain attached to the microneedles or be subsequently removed. The active component can facilitate biochemical, optical, electrical, or physical measurements of a fluid injected or extracted by the needle device.

32 Claims, 10 Drawing Sheets

U.S. PATENT DOCUMENTS

| | | | |
|---|---|---|---|
| 4,894,664 A | 1/1990 | Tsung Pan | |
| 4,922,265 A | 5/1990 | Pan | |
| 4,972,204 A | 11/1990 | Sexton | |
| 5,194,877 A | 3/1993 | Lam et al. | |
| 5,199,487 A | 4/1993 | DiFrancesco et al. | |
| 5,249,358 A | 10/1993 | Tousignant et al. | |
| 5,283,179 A * | 2/1994 | Wood | 435/8 |
| 5,311,896 A | 5/1994 | Kaartinen | |
| 5,312,456 A | 5/1994 | Reed et al. | |
| 5,443,713 A | 8/1995 | Hindman | |
| 5,457,041 A * | 10/1995 | Ginaven et al. | 435/455 |
| 5,484,399 A * | 1/1996 | DiResta et al. | 604/21 |
| 5,591,139 A * | 1/1997 | Lin et al. | 604/264 |
| 5,685,491 A | 11/1997 | Marks et al. | |
| 5,801,057 A * | 9/1998 | Smart et al. | 436/68 |
| 5,852,495 A * | 12/1998 | Parce | 356/344 |
| 5,871,158 A | 2/1999 | Frazier | |
| 5,876,582 A | 3/1999 | Frazier | |
| 5,928,207 A * | 7/1999 | Pisano et al. | 604/272 |
| 6,009,347 A * | 12/1999 | Hofmann | 604/21 |
| 6,232,107 B1 * | 5/2001 | Bryan et al. | 435/189 |
| 6,267,858 B1 * | 7/2001 | Parce et al. | 204/600 |
| 6,334,856 B1 * | 1/2002 | Allen et al. | 604/191 |

* cited by examiner

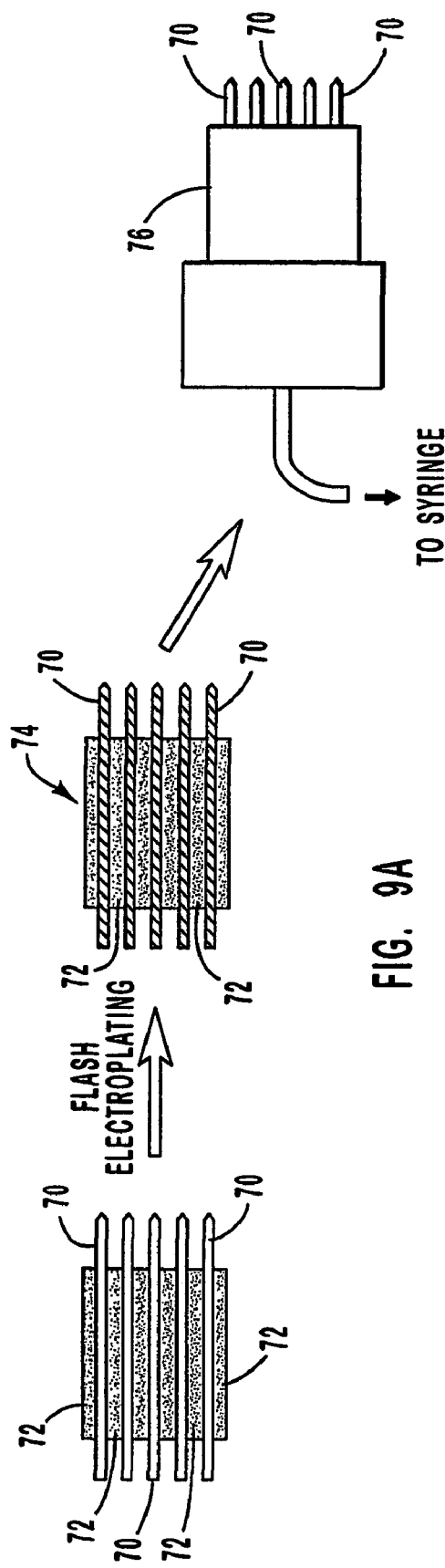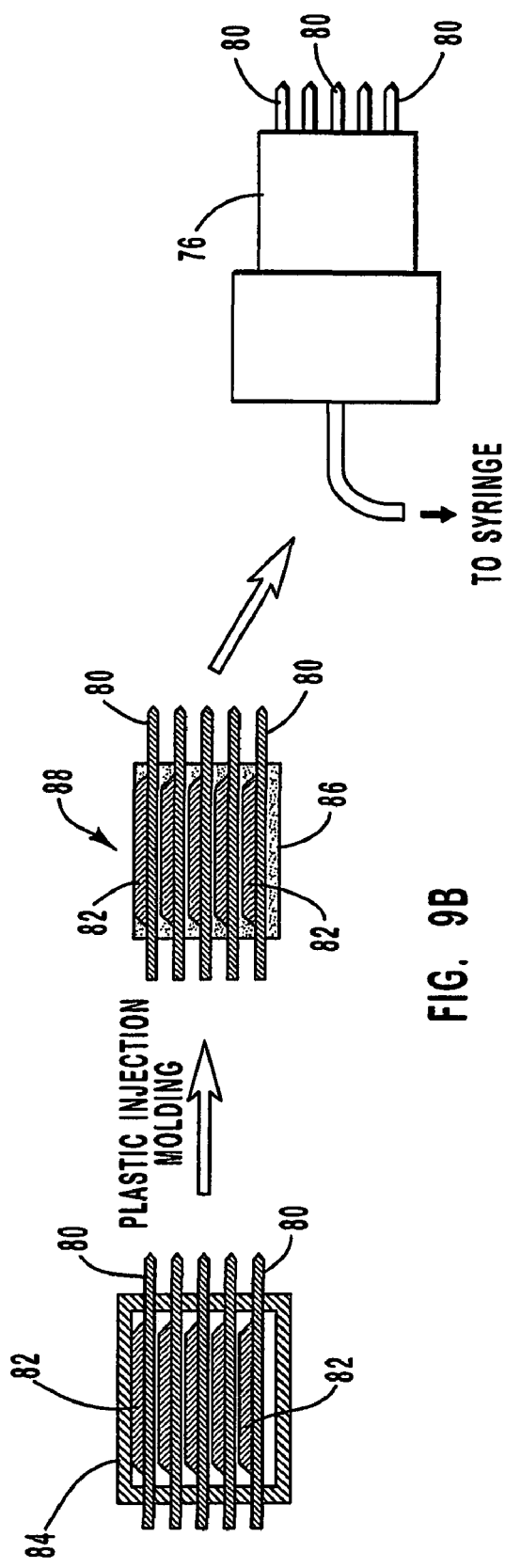

ACTIVE NEEDLE DEVICES WITH INTEGRATED FUNCTIONALITY

BACKGROUND OF THE INVENTION

1. Field of the Invention

The present invention relates generally to needle devices for the injection and extraction of fluids. More specifically, the present invention relates to active needle devices such as macroneedles, microneedles, and macroneedle or microneedle arrays which have one or more active components providing additional functionality to the needle devices.

2. Relevant Technology

Micro instrumentation is a rapidly growing area of interest for a broad spectrum of applications. One particularly fast growing area is biomedical instrumentation where significant efforts are being made to develop micro biochemical analysis systems, physiological analysis systems, and drug delivery systems. A variety of manufacturing technologies are used to fabricate these micro systems, many of which are categorized under the set of technologies known as micromachining. The number of biomedical applications for micromachining technologies is rapidly growing. Since micromachining technologies are relatively new, there is an increasing set of manufacturing techniques and critical applications still to be addressed.

It is well known that needles are used to extract samples of substances from living tissue in order to analyze the substances for diagnostic purposes, or to deliver a drug or medicament. The majority of needles in use today are macroneedles, which have a relatively large diameter as compared to a blood cell and are on the order of millimeters (mm).

In many areas of biotechnology and medicine, there exists the need for fluid injection or extraction on a microscale; either for injection into a precise location, or for injecting or extracting small amounts of fluid. It is advantageous to be able to perform these injections or extractions with a minimal amount of tissue damage, and also with a minimum amount of discomfort and pain to patients. Microneedles and microneedle arrays are capable of performing these tasks. For example, microneedles and microneedle arrays can be used as precise injection/extraction needles in cell biology, as injection/extraction heads in a drug delivery system or microchemical factory, and as injection/extraction heads in microsurgery. Some of the smallest hollow needles that are currently available have inner diameters of over 200 µm. Prior micro-sized (sizes on the order of microns, where 1 micron=1 µm=$10^{-6}$ m) needles include those disclosed in U.S. Pat. No. 5,457,041 to Ginaven et al., and U.S. Pat. No. 5,591,139 to Lin et al.

For some applications, it is desirable to inject small amounts of fluid; however, in other situations, larger amounts of fluid are required to be injected. Most of the prior systems do not have the capability to transmit larger amounts of fluid into a precise location. One of the methods used to address this problem is to fabricate an array of needles, as in U.S. Pat. No. 5,457,041 referred to hereinabove, which discloses an array of microneedles of about 20 needles by 20 needles, wherein the length of the needles is between 10 and 25 microns, and the spacing between needles is between about 5 and 20 microns.

In U.S. Pat. No. 5,591,139 referred to above, silicon-based microneedles are disclosed which are fabricated using integrated circuit processes. Various devices such as microheaters, mircrodetectors, and other devices can be fabricated on the microneedle.

Problems with prior microneedles include relatively poor mechanical durability. This is mainly due to the fact that such microneedles have been made out of etched silicon or out of chemical vapor deposited polysilicon, both of which have a tendency to be brittle and break easily.

In some cases, it is desirable to analyze the fluids being injected or extracted by the microneedle(s). Prior microneedles generally have been separate from the systems used to analyze (chemically, optically, or otherwise) the fluids. In these cases, having a separate analysis system can require additional equipment and is costly, complex, and inconvenient.

It would therefore be of substantial interest to develop a durable needle device which is capable of injecting or extracting precise quantities of fluids into specific locations with a minimal amount of tissue damage, and which has integrated sensing capabilities.

SUMMARY OF TH INVENTION

Active needle devices of the present invention have integrated functionalities such as biochemical, electrical, or optical sensing capabilities. The active needle devices can be active macroneedles or microneedles, as well as active macroneedle or microneedle arrays, which incorporate biosensors therein such as for monitoring metabolic levels.

In one embodiment of the invention, an active needle device for fluid injection or extraction includes at least one hollow elongated shaft defining at least one channel therethrough. The channel provides communication between at least one input port and at least one output port of the needle device. At least one active component such as a sensor or actuator is placed or integrated into the elongated shaft. The needle device can be a macroneedle, a microneedle, or an array of macroneedles or microneedles. The microneedles can be fabricated on a substrate which can remain attached to the microneedles or can be subsequently removed. The active component can facilitate biochemical, optical, electrical, or physical measurements of a fluid injected or extracted by the needle device.

Two- or three-dimensional microneedle arrays can be constructed having cross-coupling flow channels that allow for pressure equalization, and balance of fluid flow within the microneedle arrays. A plurality of mechanical support members can be integrated into the arrays for stability and to control the penetration depth of the microneedles. In addition, an active microneedle or microneedle array may include various functionalities such as integrated biochemical sensors, as well as electrical, optical, or mechanical transducers and sensors. The sensors reduce or eliminate the requirement for additional external analysis equipment and enhance overall device portability, disposability, and compactness.

The active microneedle and microneedle arrays of the invention are particularly useful for fluid extraction and analysis. In one embodiment, an active microneedle or microneedle array includes biochemical sensing reagents which are deposited on an inner surface of the microneedle(s), with a window provided on a surface of the microneedle(s) for the detection of bioluminescence which occurs in the presence of certain metabolic substances.

A method of fabricating an active microneedle device according to the present invention includes providing a substrate with a substantially planar surface and depositing a metal material on the planar surface to form one or more bottom walls for one or more microneedles. A top surface of the bottom walls is coated with a photoresist layer to a height corresponding to a selected inner height of a microchannel for each of the microneedles. A metal material is then deposited to form side walls and a top wall upon the bottom walls and around the photoresist layer. The photoresist layer is then removed from each microchannel to form the microneedles. The microneedles can be released from the substrate and used independently of the substrate, if desired.

The method of fabricating the active microneedle device can include p+ etch-stop membrane technology, anisotropic etching of silicon in potassium hydroxide, sacrificial thick photoresist micromolding technology, and micro-electrodeposition technology. For a biochemical luminescence sensing microneedle device, certain biochemical sensing reagents can be drawn into and dried onto the inner walls of the hollow needle(s).

The active needle devices of the invention have the advantage of permitting real-time analysis of a fluid being sampled. In addition, the array of active microneedles are capable of injecting or extracting relatively large quantities of fluids with minimal tissue damage and can be readily attached to a standard syringe. The array of active microneedles or a single active microneedle can also be easily and economically fabricated. Yet another advantage of the array of active microneedles or a single active microneedle is a high degree of mechanical durability.

These and other features of the present invention will become more fully apparent from the following description, or may be learned by the practice of the invention as set forth hereinafter.

BRIEF DESCRIPTION OF THE DRAWINGS

In order to more fully understand the manner in which the above recited and other advantages of the invention are obtained, a more particular, description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 9A and 9B depict alternative methods of assembling two-dimensional needle arrays into three-dimensional needle array devices;

DETAILED DESCRIPTION OF THE INVENTION

The present invention is directed to active needle devices, such as macroneedles, microneedles, and macroneedle or microneedle arrays, which have one or more active components incorporated therein providing additional functionality to the needle devices. An active needle device according to the invention generally includes at least one hollow elongated shaft defining at least one channel therethrough. The channel provides communication between at least one input port and at least one output port of the needle device. At least one active component such as a sensor or actuator is placed or integrated into the elongated shaft. The active component can facilitate biochemical, optical, electrical, or physical measurements of a fluid injected or extracted by the needle device. The active component also reduces or eliminates the requirement for additional external analysis equipment, and enhances the overall device portability, disposability, and compactness.

Figure 1A:
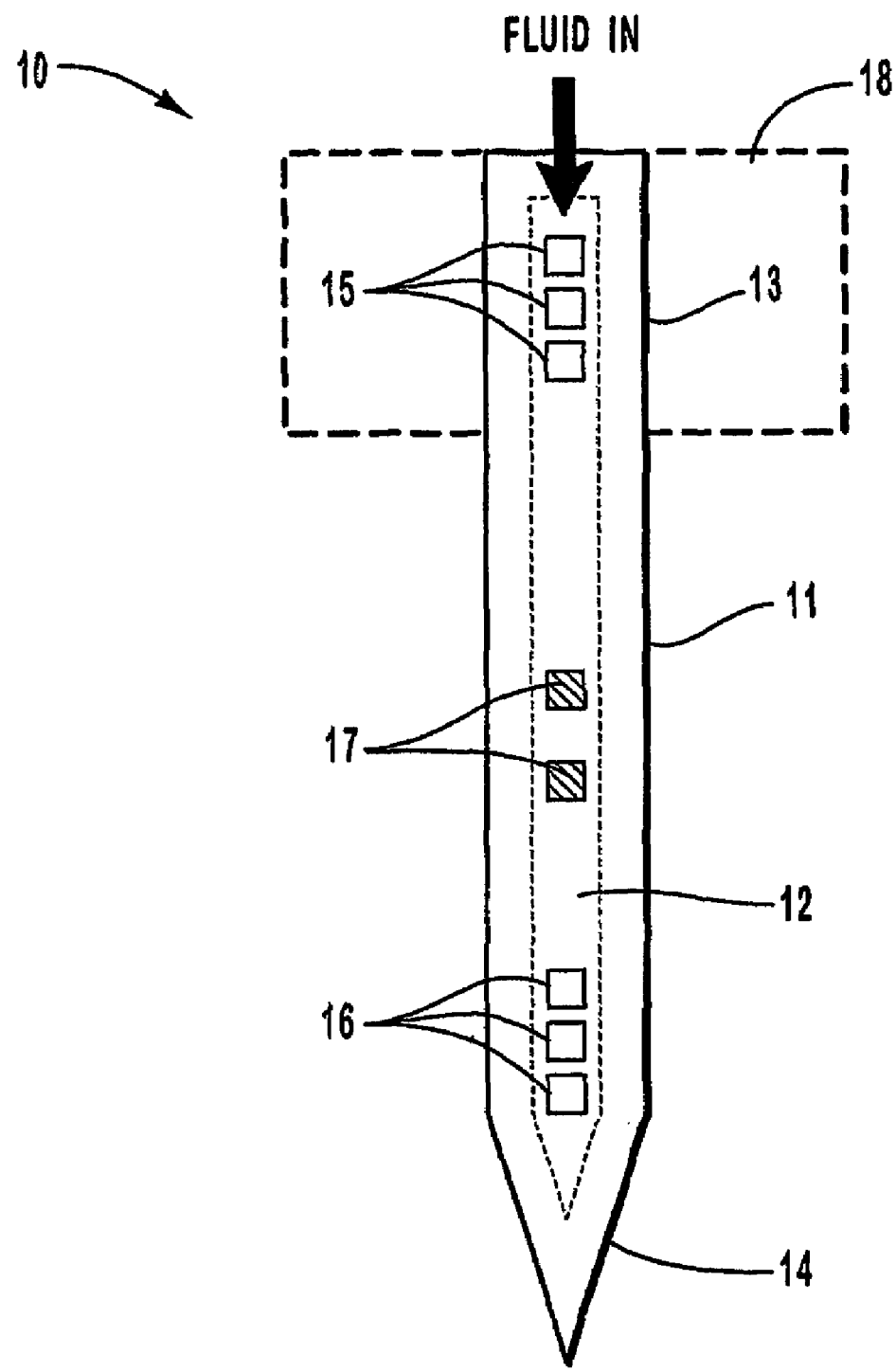
FIG. 1A is a schematic representation of a single active needle device according to the present invention.

Referring to the drawings, wherein like structures are provided with like reference designations, FIG. 1A is a schematic representation of a single active needle device 10 according to one embodiment of the present invention. The needle device 10 includes a hollow elongated shaft 11 defining a single channel 12 from a proximal inlet end 13 to a distal tip end 14 which is tapered. One or more input ports 15 are located at the proximal inlet end 13 of elongated shaft 11 and one or more output ports 16 are located toward the distal tip end 14. The channel 12 provides communication between input ports 15 and output ports 16.

The needle device 10 can be either a macroneedle or a microneedle, depending on the configuration of elongated shaft 11 defining channel 12. A "macroneedle" as used herein means any conventional type needle used to inject or extract fluids, such as conventional metallic needles used in medical applications. A "microneedle" as used herein means any micro-sized needle which can be generally fabricated by micromachining techniques.

At least one active component 17 is placed or integrated directly in elongated shaft 11. The active component 17 can include one or more electronic components, electromechanical components, mechanical components, biochemical components, or various combinations thereof. These components can be configured to form one or more sensors, actuators, or combinations thereof For example, the sensors can be a biosensor, such as a bioluminescence-based biosensor, which is discussed in further detail hereafter, microdetectors, optical pressure sensors, DNA analyzer chips, and the like. The actuators can include electromechanical components for fluid manipulation such as micropumps, microvalves, or the like.

In addition, active component 17 can include an integrated circuit chip, an optical detector, other electrical based components, impedance analyzers (e.g., integrated resistance, inductance, and capacitance sensors), transducers, and the like. A transducer can be used for detection of fluid parameters such as flow velocity, temperature, pressure, etc. The active component 17 can facilitate one or more biochemical, optical, electrical, or physical, measurements or other analyzing functions for a fluid injected or extracted by needle device 10.

The active component 17 can be interfaced electronically with conventional analyzing equipment or can be a stand alone device. In addition, the active component 17 may be fabricated independently of the needle device and subsequently placed therein, or may in some cases be fabricated at the same time as the needle device. If fabricated independently, the active component can be made on separate chips, which can be affixed to an internal surface of the needle or substituted for part of a wall of the needle. Additional details related to active component 17, including specific embodiments thereof, are discussed below.

The active component 17 allows the needle device to provide real-time analysis of a fluid being sampled such as in a blood analysis system. For example, blood can be analyzed by an on-chip amplifier, such as a blood analysis amplifier, and an A/D converter which converts an analog signal to a digital signal for transmission to a computer for real-time computer analysis.

Figure 1B:
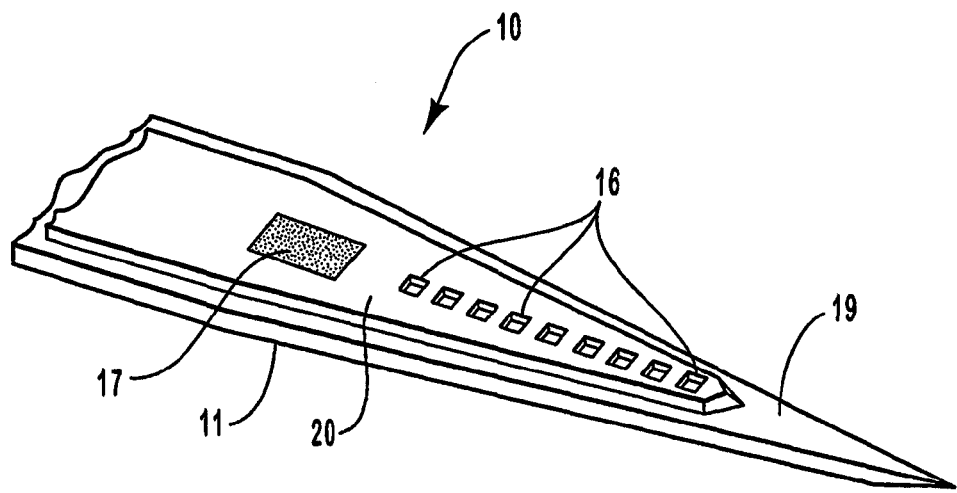
FIG. 1B is a schematic representation of a portion of a single active needle device in the form of a microneedle according to one embodiment of the present invention.

When needle device 10 is configured as a single microneedle, elongated shaft 11 generally includes a bottom wall formed by a solid layer 19, and opposing side walls connected by a top wall which are formed by a hollow layer 20, as shown in FIG. 1B. These bottom, side, and top walls define channel 12 in the form of a microchannel with a transverse cross-sectional profile that is substantially rectangular. The microneedle optionally has a flange 18 at proximal inlet end 13 (FIG. 1A) which functions as a structural support for the microneedle. The flange 18 can control penetration depth and can be used to mechanically fix the microneedle to a surface that is penetrated. The input ports 15 located at proximal inlet end 13 and output ports 16 are formed in one or more of the bottom wall, side walls, or top wall of the microneedle. The input ports 15 and output ports 16 in the microneedle can be formed by conventional fabrication processes such as etching. FIG. 1B shows active component 17 such as a biosensor adjacent to output ports 16.

The microneedle can be fabricated by micromachining techniques from a variety of metallic materials such as nickel, copper, gold, silver, platinum, palladium, titanium, chromium, alloys thereof, and the like, as well as other materials such as silicon, polysilicon, ceramics, glass, carbon black, plastics, composites thereof, etc. In one embodiment, the microneedle is fabricated from a non-silicon material such as any of the above metallic materials using the micromachining techniques discussed in further detail below. The microneedle can be fixed on a substrate where fabricated or can be removed from a substrate after fabrication.

Figure 2A:
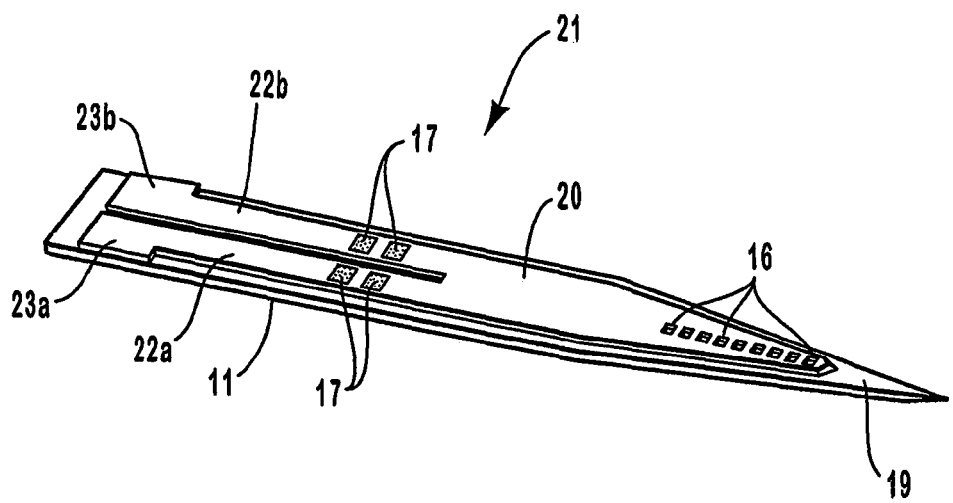
FIGS. 2A and 2B are schematic depictions of multi-lumen active microneedles according to alternative embodiments of the present invention.
Figure 2B:
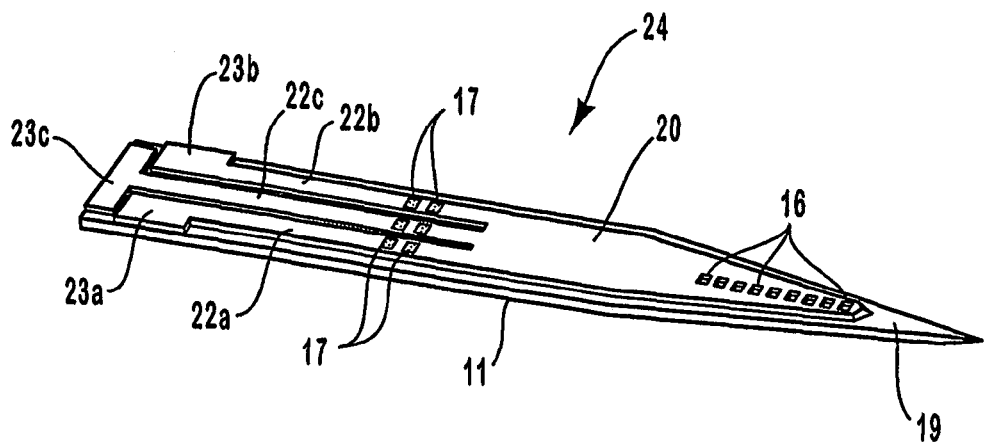

FIGS. 2A and 2B are schematic depictions of multi-lumen active microneedles according to alternative embodiments of the present invention. FIG. 2A illustrates a dual-lumen active microneedle 21 which is constructed in a similar manner as the microneedle of FIG. 1B, having an elongated shaft 11 including a bottom wall formed by a solid layer 19, and opposing side walls connected by a top wall which are formed by a hollow layer 20. The hollow layer 20 is configured such that microneedle 21 has two microchannel members 22a and 22b each with a lumen therein and each with corresponding inputs 23a and 23b. One or more active components 17 such as biosensors are located in each of microchannel members 22a and 22b.

FIG. 2B illustrates a tri-lumen active microneedle 24 which is constructed in a similar manner as microneedle 21. The microneedle 24 has an elongated shaft 11 including a bottom wall formed by a solid layer 19, and opposing side walls connected by a top wall which are formed by a hollow layer 20. The hollow layer 20 is configured such that microneedle 24 has three microchannel members 22a, 22b, and 22c therein, each with corresponding inputs 23a, 23b, and 23c. One or more active components 17 such as biosensors are located in each of microchannel members 22a, 22b, and 22c.

The multi-lumen active microneedles according to the present invention allow two or more different fluids to be delivered by the microneedle, which are mixed just before delivery. The multi-lumen active microneedles can also be used to separately distribute an extracted fluid for multiple analyses.

Figure 3:
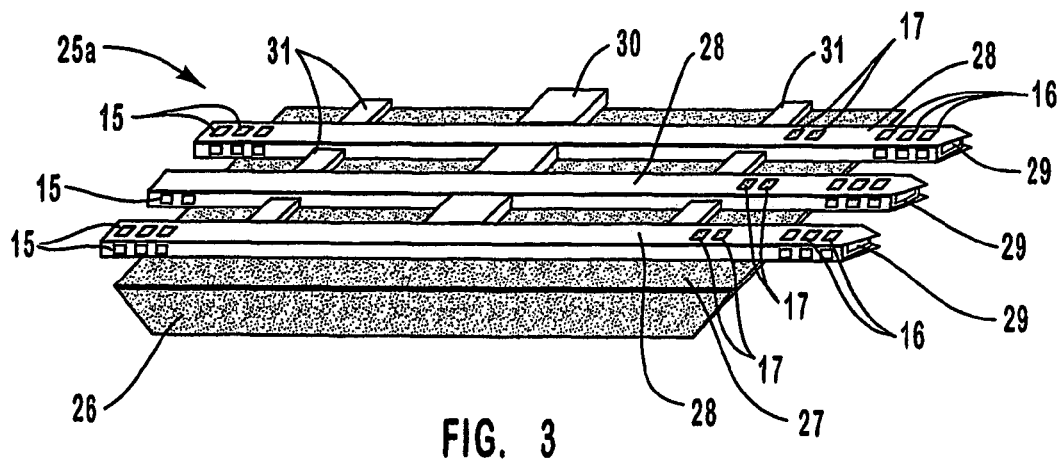
FIG. 3 is a schematic representation of microneedles in a two-dimensional array according to a further embodiment of the present invention.

FIG. 3 is a schematic depiction of an active microneedle array 25a according to another embodiment of the invention. The microneedle array 25a is formed in a two-dimensional configuration on a substrate 26 having a substantially planar upper surface 27. The substrate 26 is preferably composed of a semiconductor material such as silicon, although other materials can be employed such as glass, metals, ceramics, plastics, and composites or combinations thereof.

A plurality of hollow microneedles 28 are formed on upper surface 27 of substrate 26. The microneedles 28 each have a bottom wall, two opposing side walls, and a top wall that define a microchannel therein. Each bottom wall is formed partially on upper surface 27 of substrate 26. The microneedles 28 each have one or more input ports 15 at a proximal end thereof. A distal portion of each microneedle 28 including the microchannels extends beyond an edge of upper surface 27 of substrate 26 in a cantilevered manner and terminates in needle tips 29 which can have a channel opening therein. In addition, one or more outlet ports 16 can be located adjacent to needle tips 29. The microneedles 28 are preferably aligned substantially parallel to each other on substrate 26. One or more active components 17, such as biosensors or other sensing or actuating devices as discussed above, are located in each of microneedles 28.

The microchannels in the microneedles 28 are preferably dimensioned to have a width between sidewalls of less than about 100 µm, and more preferably about 0 µm to about 50 µm. When the width is zero between the sidewalls, the microneedles 28 effectively become one multilumen microneedle with a plurality of microchannels as shown in FIGS. 2A and 2B. The height between the top and bottom walls of the microchannel is also preferably less than about 100 µm, and more preferably about 2 µm to about 50 µm. The length of each microneedle can be from about 0.05 µm to about 5 mm, and the width of each microneedle can be from about 0.05 µm to about 1 mm. The center-to-center spacing between individual microneedles can be from about 50 µm to about 200 µm. The microneedles can also withstand flow rates of up to about 1.5 cc/sec.

The microneedle length extended from substrate 26 can be varied from less than about 50 µm (subcutaneous) to several millimeters for fluid delivery/extraction. For example, the distal end of each microneedle 28 can extend beyond the edge of substrate 26 a distance from about 10 µm to about 100 mm. The inner cross-sectional dimensions of the microchannels in individual microneedles can range from about 10 µm to about 1 mm in width and from about 2 µm to about 50 µm in height.

Accordingly, the microchannel in each of the microneedles can have a cross-sectional area in the range from about 25 µm² to about 5000 µm².

A needle coupling channel member 30 can be optionally formed on upper surface 27 of substrate 26 between microneedles 28. The coupling channel member 30 has a bottom wall, two opposing side walls, and a top wall that define a coupling microchannel therein, which provides for fluid communication between the microchannels of each microneedle 28. The coupling channel member 30 also allows for pressure equalization and balance of fluid flow between microneedles 28.

structural support members 31 can be formed on either side of coupling channel member 30 on upper surface 27 of substrate 26. The structural support members 31 mechanically interconnect microneedles 28 to provide rigidity and strength to microneedle array 25a. The support members 31 also precisely control the penetration depth of microneedles 28.

The microneedles 28, coupling channel member 30, and support members 31 can be formed from a variety of metal materials such as nickel, copper, gold, palladium, titanium, chromium, alloys or combinations thereof, and the like, as well as other materials such as silicon, polysilicon, ceramics, glass, carbon black, plastics, composites or combinations thereof, and the like. The microneedles 28 can be in fluid communication with a single fluid input device or with multiple fluid input devices (not shown).

Figure 4:
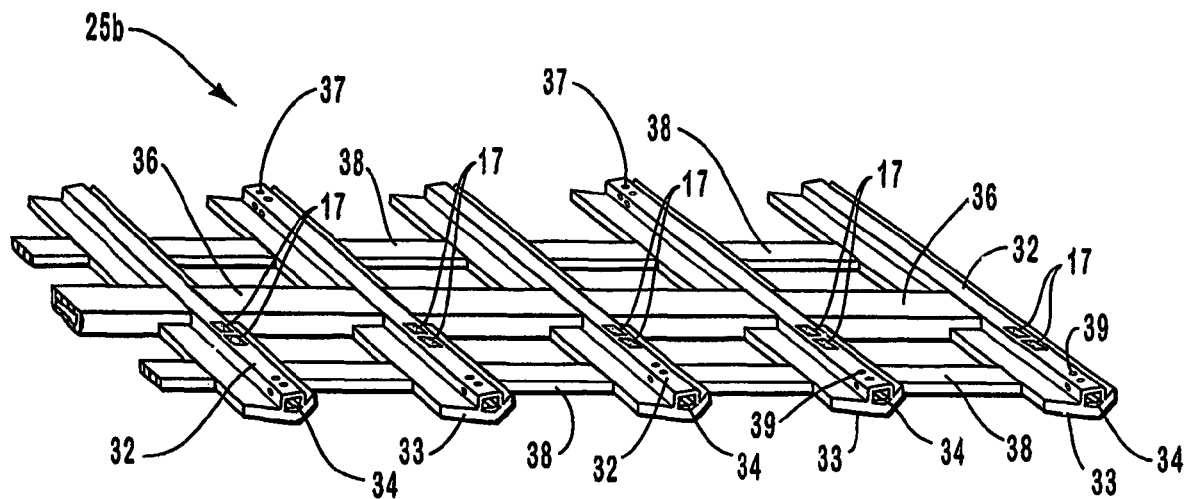
FIG. 4 is a schematic representation of microneedles in a two-dimensional array according to another embodiment of the present invention.

An active microneedle array 25b according to an alternative embodiment of the invention is shown in FIG. 4. The microneedle array 25b has a two-dimensional configuration with similar components as microneedle array 25a discussed above, except that the substrate has been removed from the array. Accordingly, microneedle array 25b includes a plurality of microneedles 32 with microchannels that are dimensioned as discussed above for microneedle array 25a.

The microneedles 32 each terminate at a needle tip 33 with a channel opening 34 therein. A needle coupling channel member 36 with a coupling microchannel therein provides a fluidic interconnection between the microchannels of each microneedle 32. A pair of structural support members 38 are formed on either side of coupling channel member 36 and interconnect with microneedles 32. One or more input ports 37 and output ports 39 can be optionally formed in microneedles 32 to increase fluid input and output flow. The input ports 37 and output ports 39 can be formed in one or more of the bottom walls, aside walls, of microneedles 32 by conventional fabrication processes such as etching. One or more active components 17, such as biosensors or other sensing or actuating devices as discussed above, are located in each of microneedles 32.

Figure 5:
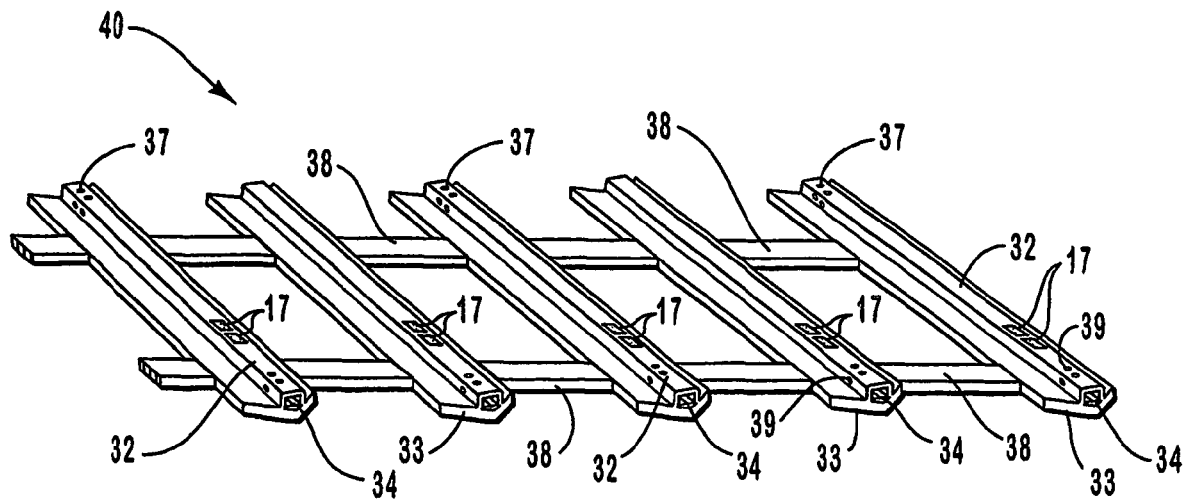
FIG. 5 is a schematic representation of microneedles in a two-dimensional array according to another embodiment of the present invention.

An active microneedle array 40 according to another embodiment of the invention is shown in FIG. 5. The microneedle array 40 has a two-dimensional configuration with similar components as microneedle array 25b, except that microneedle array 40 is formed without a coupling channel member. Accordingly, microneedle array 40 includes a plurality of microneedles 32 with microchannels that are dimensioned as discussed above for microneedle array 25a. The microneedles 32 each terminate at a needle tip 33 with a channel opening 34 therein. A pair of structural support members 38 interconnect with microneedles 32. One or more input ports 37 and output ports 39 can be optionally formed in microneedles 32 to increase fluid input and output flow. One or more active components 17, such as biosensors or other sensing or actuating devices as discussed above, are located in each of microneedles 32.

Figure 6A:
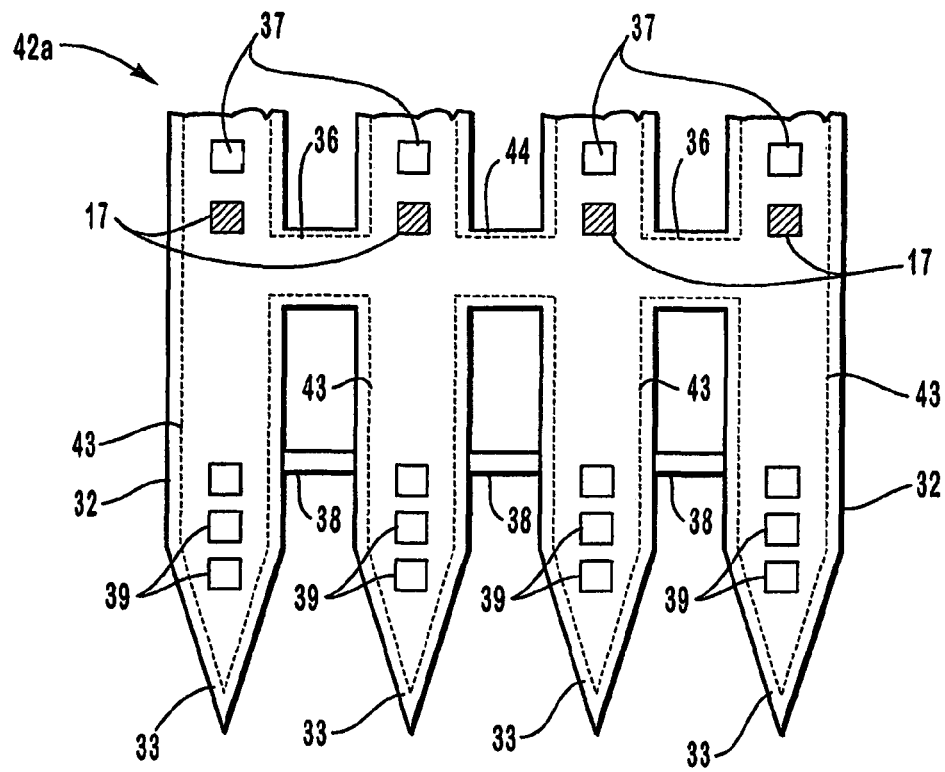
FIGS. 6A-6B are schematic depictions of single-lumen active microneedle arrays according to alternative embodiments of the present invention.

FIGS. 6A-6B and 7A-7B are schematic depictions of single and multi-lumen active microneedle arrays according to alternative embodiments of the present invention. An active microneedle array 42a is shown in FIG. 6A having a two-dimensional configuration with similar components as microneedle array 25b discussed above. Accordingly, microneedle array 42a includes a plurality of microneedles 32 each with single lumen microchannels 43. The microneedles 32 each terminate at a needle tip 33. A needle coupling channel member 36 with a coupling microchannel 44 therein provides a fluidic interconnection between microchannels 43 in each microneedle 32. A structural support member 38 interconnects microneedles 32. One or more input ports 37 and output ports 39 are located in microneedles 32. One or more active components 17 are located in each of microneedles 32.

Figure 6B:
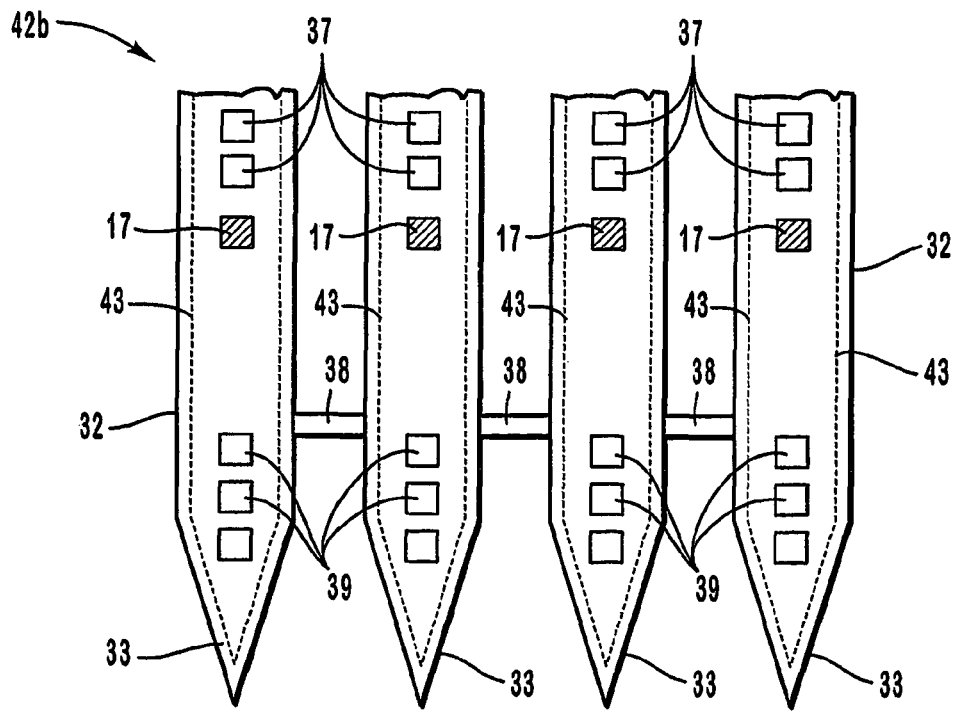

Another active microneedle array 42b is shown in FIG. 6B. The microneedle array 42b has a two-dimensional configuration with similar components as microneedle array 42a, except that microneedle array 42b is formed without a coupling channel member. Accordingly, microneedle array 42b includes a plurality of microneedles 32 each with single lumen microchannels 43. The microneedles 32 each terminate at a needle tip 33 and a structural support member 38 interconnects microneedles 32. One or more input ports 37 and output ports 39 are located in microneedles 32, and one or more active components 17 are located in each of microneedles 32.

Figure 7A:
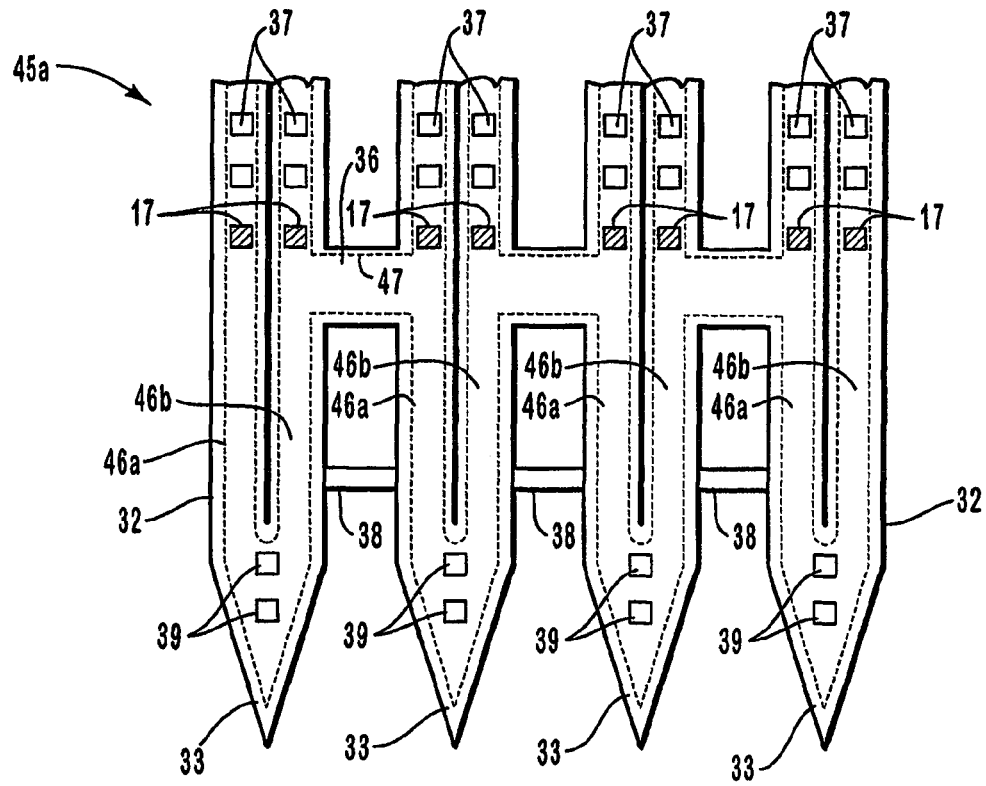
FIGS. 7A-7B are schematic depictions of multi-lumen active microneedle arrays according to alternative embodiments of the present invention.

FIG. 7A depicts an active microneedle array 45a having a two-dimensional configuration with similar components as microneedle array 42a discussed above, except that microneedle array 45a has a duel lumen microchannel configuration. Accordingly, each microneedle 32 in array 45a is constructed to have a pair of microchannels 46a and 46b. A needle coupling channel member 36 with a coupling microchannel 47 therein provides a fluidic interconnection between microchannels 46a and 46b in each microneedle 32. One or more input ports 37 and output ports 39 are located in microneedles 32, and one or more active components 17 can be located in each microchannel of microneedles 32.

Figure 7B:
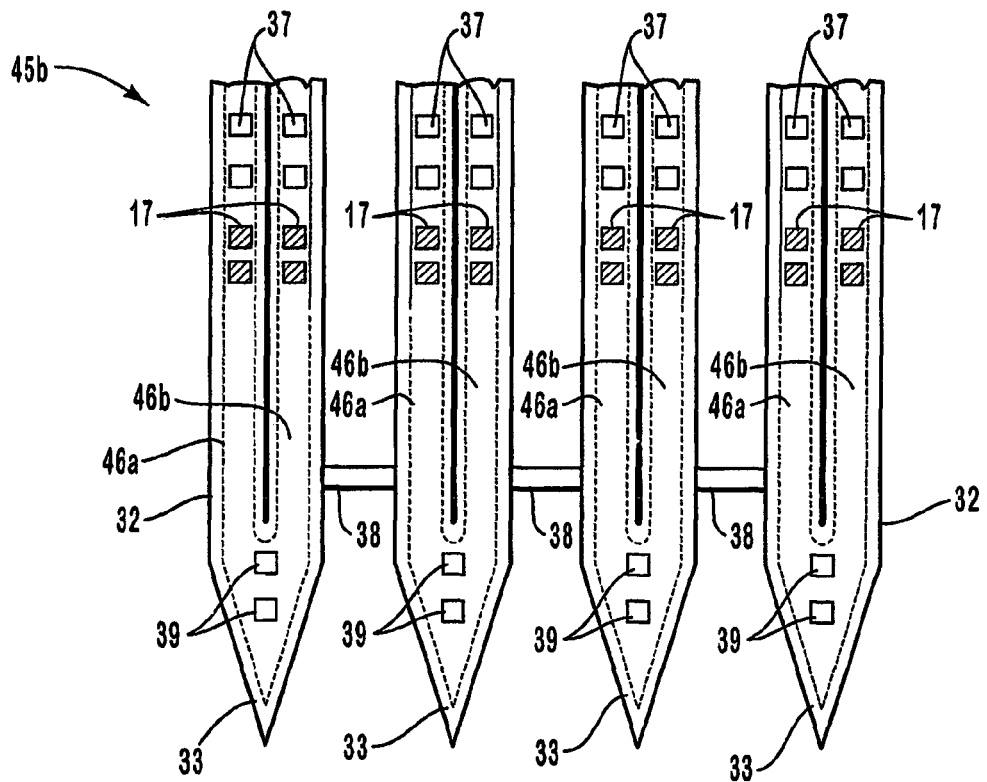

FIG. 7B depicts an active microneedle array 45b having a two-dimensional configuration with similar components as microneedle array 42b discussed above, except that microneedle array 45b has a duel lumen microchannel configuration. Accordingly, each microneedle 32 in array 45b is constructed to have a pair of microchannels 46a and 46b. A structural support member 38 interconnects microneedles 32, and one or more input ports 37 and output ports 39 are located in microneedles 32. One or more active components 17 can be located in each microchannel of microneedles 32.

In other alternative embodiments, active microneedle arrays can be fabricated to have additional microchannels in each microneedle. For example, each microneedle in the array can have a tri-lumen channel construction such as shown for the microneedle of FIG. 2B discussed above.

It should be understood that the above discussion related to microneedle arrays is equally applicable to macroneedles, which can be configured in various arrays. The macroneedle arrays can have similar structures as described above for the microneedle arrays such as single or multi-lumen channel configurations, multiple input and output ports, structural support members, coupling channel members, and active components in the macroneedles.

Figure 8A:
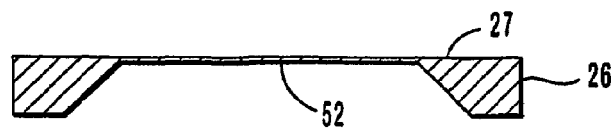
FIGS. 8A-8F schematically depict the fabrication process sequence for forming a microneedle array.

A method of fabricating a two-dimensional microneedle array according to the invention is depicted schematically in FIGS. 8A-8F. As shown in FIG. 8A, a substrate 26 having a substantially planar surface 27 is provided, such as a silicon wafer which is polished on both sides. The wafer can have a thickness of about 1 µm to about 700 µm, and is preferably about 150 µm thick. One side of the wafer is heavily doped with boron using high temperature thermal diffusion in order to form a 3-5 µm thick p+ layer. Next, silicon nitride ($Si_3N_4$) is deposited on both sides of the wafer using plasma-enhanced chemical vapor deposition (PECVD). The silicon nitride on the undoped side of the wafer is patterned and etched employing photoresist as a mask, and then isotropic etching (a $CF_4$ plasma for example) is used to etch the exposed silicon nitride to define the area upon which the microneedles are to be fabricated. After patterning the silicon nitride layer, the exposed silicon is anisotropically etched using a potassium hydroxide (KOH) solution. The p+ boron layer serves as an etch stop, resulting in a thin sacrificial membrane 52, as shown in FIG. 8A. The sacrificial membrane 52 comprises the surface upon which the microneedles are formed and then subsequently released as described below.

Figure 8B:
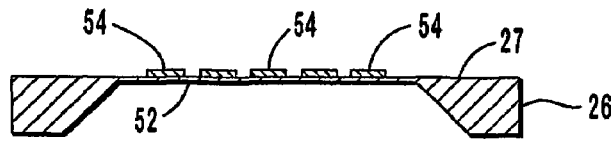

Next, a metal system of adhesion layers and an electroplating seed layer are deposited (by electron beam evaporation, for example) onto the insulating silicon nitride film. The adhesion and seed layers are typically composed of, but not limited to, titanium, chromium, copper, or combinations thereof. Then, using a mask of the appropriate dimensions and standard photolithographic techniques, this metal multi-layer is patterned. A metal material is then electroplated to form one or more bottom walls 54 (e.g., about 20 µm thick) for the microneedles, as shown in FIG. 8B. Palladium is one preferred metal for the bottom wall since it provides high mechanical strength and durability, is corrosion resistant, provides biocompatibility for use in biomedical applications, and is easily electroplated to within precise dimensions. Other materials which fit the criteria mentioned could also be used equally well, such as copper, nickel, or gold. When performing the electroplating, the bath chemistry and the electroplating conditions (such as amount of applied current and time in the electroplating bath) should be precisely controlled for optimum results. The typical dimensions for bottom walls 54 are about 10-20 µm in thickness, and about 50 µm wide.

Figure 8C:
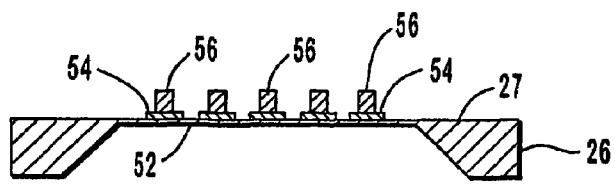

After bottom walls 54 have been formed, a commercially available thick photoresist is deposited (e.g., about 20 µm thick) and patterned using ultraviolet exposure and alkaline developer, resulting in sacrificial layers 56 as depicted in FIG. 8C. Next, a metal seed layer such as gold is sputter deposited (e.g., about 800 Å thick) onto the photoresist sacrificial layers 56. The metal seed layer serves as an electrical contact for the subsequent metal electroplating.

Figure 8D:
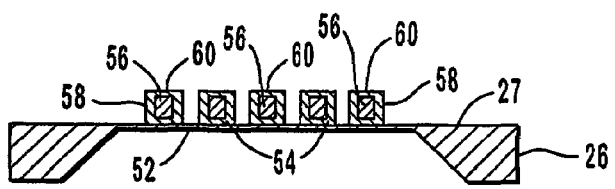
Figure 8E:
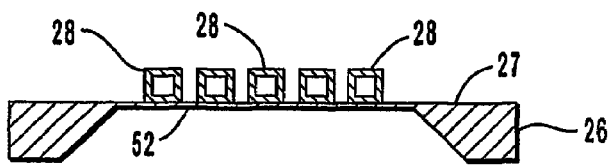

A metal layer such as palladium is then electroplated (e.g., about 20 µm thick) onto sacrificial layers 56 to form a plurality of side walls 58 and top walls 60 of each microneedle, as shown in FIG. 8D. The exposed metal seed layer is then removed using wet etching techniques to expose the underlying photoresist. Once the metal seed layer has been etched, the wafer is placed in an acetone bath to remove the photoresist from inside the microneedle structures, thereby producing a plurality of hollow microneedles 28, as shown in FIG. 8E.

Figure 8F:
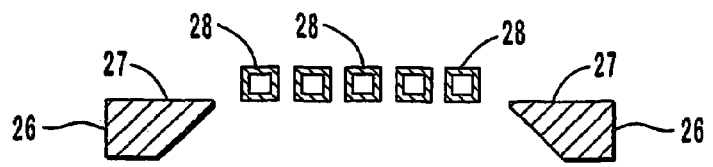

In the final processing step, sacrificial membrane 52 is removed by an isotropic etching technique, such as reactive ion etching in a $SF_6$ plasma. Thus, the microneedle ends are released from sacrificial membrane 52 and are freely suspended, projecting outward from substrate 26, as depicted in FIG. 8F and in the embodiment of FIG. 3.

Figure 8G:
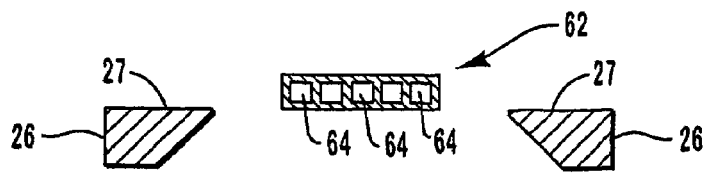
FIG. 8G depicts an embodiment of a multilumen microneedle formed according to the present invention.

Alternatively, the fabricating method outlined above can be used to form a multilumen microneedle by forming bottom walls 54 with zero spacing therebetween on substrate 26 and carrying out the remaining steps as described above. A resulting multilumen microneedle 62 with a plurality of microchannels 64 therein is shown in FIG. 8G.

In an alternative fabrication method, the microneedle array can be released from substrate 26 following surface fabrication on substrate 26, such as for the embodiment shown in FIG. 4. This method does not require sacrificial membrane formation or KOH etching. Instead, the needle arrays are released using wet etching of the seed metal from underneath the needle structures. If the seed metal is copper, for example, then this can be done by a selective etch of ammonium hydroxide saturated with cupric sulfate.

Arrays of two up to hundreds of microneedles can be easily and economically fabricated in a package with dimensions on the order of millimeters according to the above procedure. A single microneedle such as shown in FIG. 1B can also be fabricated according to the procedure outlined above. In addition, instead of having the fluid outlet at the tips of the microneedles, fluid outlet ports can be etched into the side walls, top walls, and/or bottom walls of the microneedles if a larger amount of fluid transfer is desired.

Using the above fabrication methods provides the flexibility to integrate many additional functions directly onto the microneedles. These fabrication methods are low temperature and are compatible with integrated circuit (IC) technology as a post process. For example, various active components such as sensors, transducers, and electronic interfaces may be fabricated as integrated components on-chip during the needle fabrication process. An example of a procedure for fabricating a microneedle with on-chip devices such as CMOS (complementary metal-oxide semiconductor) devices is disclosed in U.S. Pat. No. 5,591,139 to Lin et al., the disclosure of which is incorporated by reference herein. Alternatively, the active components may be in the form of prefabricated chips which are subsequently placed within the needle channels.

All of the needle devices including microneedles and arrays of the present invention can be coated on the inside with biocompatible materials, such as silicon nitride, gold, plastics, etc., by conventional coating processes known to those skilled in the art.

In addition, a light enhancing reflective coating can be formed on the inner surfaces of the active needle devices defining the lumens therein. The reflective coating can enhance the light output generated during a bioluminescent reaction in a bioluminescent-based active needle to provide for more sensitive biosensing capabilities. Suitable reflective materials that can be used to coat the inner surfaces of the needle devices include silver, chromium, titanium, platinum, combinations thereof, and the like. Increased light intensity has also been observed for long narrow channels, which can be used to effectively design a bioluminescent-based microneedle. Further details related to light enhancement of micro reaction chambers and long narrow (micro) channels are described in Bartholomeusz et al., "BIOLUESCENT BASED BIOSENSOR FOR POINT-OF-CARE DIAGNOSTICS," First Annual International IEEE Conference on Microtechnology, Medicine, and Biology, Lyon, France, Oct. 12-14, 2000, the disclosure of which is incorporated by reference herein.

FIGS. 9A and 9B depict alternative methods of assembling two-dimensional needle arrays into three-dimensional needle array devices. In the method depicted in FIG. 9A, a plurality of two-dimensional microneedle arrays 70 are provided which have been released from a substrate as shown for the array of FIG. 4. The microneedle arrays 70 are positioned in a stacked configuration with a plurality of metallic spacers 72 therebetween to define the distance between any two microneedle arrays in the stack. The stacked needle array configuration is then subjected to flash electroplating to join microneedle arrays 70 with metallic spacers 72 in a fixed three-dimensional needle array device 74. The needle array device 74 can then be disposed in a machined interface structure 76, such as an acrylic interface, allowing connection to a dispensing means for injecting a liquid such as a syringe.

In the method depicted in FIG. 9B, a plurality of two-dimensional microneedle arrays 80 are provided on substrates 82 such as shown for the microneedle array of FIG. 3. The microneedle arrays 80 are positioned in a stacked configuration, with substrates 82 acting as spacers between arrays 80, to define the distance between any two microneedle arrays in the stack. The stacked array configuration is placed in a mold 84 such as an aluminum mold for plastic injection molding. The stacked array configuration, is then subjected to plastic injection molding. This bonds microneedle arrays 80 together with a plastic molding material 86, thereby forming a fixed three-dimensional needle array device 88. The array device 88 can then be disposed in an interface structure 76 allowing connection to a dispensing device such as a syringe.

In another alternative method of assembling two-dimensional needle arrays into three-dimensional needle array devices, the two dimensional arrays are manually assembled under a microscope. The two-dimensional arrays are stacked with spacers or with substrates on the arrays and are bonded together with a polymeric adhesive such as a UV-curable adhesive to form a three-dimensional needle array device, which can then be disposed in an interface structure.

The fabricated three-dimensional needle array devices are typically dimensioned to have a length of about 5 mm, a width of about 5 mm, and a height of about 2 mm.

The interface structures for connection to a syringe can be made from a variety of plastic materials such as acrylics, polystyrene, polyethylene, polypropylene, and the like. The interface structure typically accommodates a three-dimensional needle array device having up to about 25 two dimensional arrays. The interface structures are bonded to the three-dimensional needle array devices with a polymeric adhesive such as a UV-curable adhesive. The interface structures are configured to accept direct syringe connection via a connection means such as a conventional Luer-lock connector. Alternatively, interface structures can be formed for a single two-dimensional array or a single microneedle so as to accept direct syringe connection via a connector such as a Luer-lock connector.

In alternative embodiments of the invention, any of the above described array embodiments can be fabricated as a slanted active needle array, with needles in the array having varying lengths. The slanted needle array allows for collection of interstitial fluid samples at different depths during sample acquisition from a patient. Additionally, the slanted needle array allows for dispensing of medicaments into a patient at multiple depths throughout and beneath the dermal layers of the skin.

Further details regarding suitable microneedle and microneedle arrays suitable for use in the present invention are described in copending application Ser. No. PCT/US99/21509, filed Sep. 17, 1999, entitled "Surface Micromachined Microneedles" and which is incorporated by reference herein.

As discussed above, one or more active components such as a biosensor can be placed or integrated directly into the needle devices of the present invention. A biosensor is basically an analytical device that converts the concentration of an analyte in a sample into an electrical signal by way of a biological sensing element intimately connected with a transducer. A particularly suitable biosensor useful in the needle devices of the invention is a bioluminescence-based biosensor, which can be employed in any of the above described embodiments. Such a biosensor can be formed by depositing biochemical sensing reagents on one or more inner walls of a needle device. For example, various bisosensing reagents can be drawn into and dried down onto the inner walls of the hollow microneedle or microneedle arrays described previously. Bioluminescence-based biosensors are particularly suitable for monitoring metabolic levels, such as the level of creatine or glucose in blood. Generally, bioluminescent detection of the biosensor output is performed at the output ports of the microneedle.

Bioluminescence-based chemical analysis has the advantages of being substantially more sensitive than conventional chromogenic (absorbance) measurements and is known to be accurate over a range of five or more orders of magnitude of concentration ranges. It is known that firefly bioluminescence occurs by enzyme-catalyzed oxidation of luciferin utilizing adenosine triphosphate (ATP). Bacteria bioluminescence is closely coupled to nicotinaminde adenine dinucleotide hydride (NADH). Bioluminescent-based chemical analysis has the potential of measuring a wide range of metabolites from smaller sample volumes.

since most metabolites in the body are within one or two reactions from ATP or NADH, they can be measured by coupling other enzyme reactions to an ATP or NADH bioluminescent reaction and measuring the light output. During the production or consumption of a metabolite of interest, enzyme linked reactions will cause the production or consumption of ATP (or NADH) through the following bioluminescent platform reactions.

The ATP platform is based on the firefly luciferase reaction:

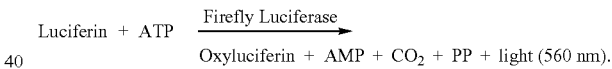

The NADH platform reaction based on NADH:FMN oxidoreductase and Bacterial Luciferase:

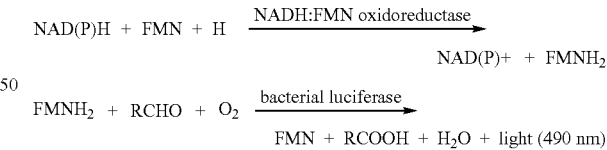

Substrates are coupled to these platform reactions through the following generic reaction:

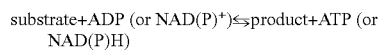

The detected changes in light intensity (measured by various light detectors as described below) will be stoichiometrically proportional to the time changing concentration of the platform molecule (ATP or NADH) and thus proportional to the metabolite of interest. The bioluminescent platform reactions can be used to measure metabolites such as L-Phenylalanine, D-Glucose, L-lactate, glucose 6-phosphate, glucose 1-phosphate, UDP-glucose, UDP-galactose, lactose, alkaline phosphatase, galactose in solution, human blood (serum & plasma), sweat, and human milk.

The light produced in the bioluminescent platform reactions can be detected by an optical detector such as a photodiode or charge coupled device (CCD). Such photosensing devices can be integrated inside a microneedle to detect the light, or can be located externally and can be used to detect the luminescence through a window in a microneedle surface. Depending on the instrument used to detect the luminescence, nanomolar, picomolar or even femtomolar analyses are possible. With increased sensitivity, smaller amounts of sample fluid are required for accurate analysis. A 0.05 micro-liter sample size that can be drawn by the microneedles can painlessly access small amounts of body fluid that can be analyzed via bioluminescence.

The transmittance of light through a medium across a certain length (l) is specified through Beer's law, $T=10^{-Absorbance}$, where $Absorbance = \epsilon_\lambda C_B (l-x)$, and $\epsilon_\lambda$ is the molar absorption coefficient in $dm^3/mole$-cm, and $C_B$ is the concentration in $mole/dm^3$. Assuming the light travels through a homogeneous medium along length $mole/dm^3$. Assuming the light travels through a homogeneous medium along length (l), the total transmitted light (T) can be expressed as:

$$T_{total(l)} = \int_{length} 10^{-\epsilon_\lambda C_B (l-x)} dx = (1-10^{-l})/Ln10$$

where $\epsilon_\lambda C_B$ is assumed to be 1 for simplicity. For a pyramid (which is the shape of the etched wells of the <100> silicon wafers), where the peak depth of the pyramid is equal to the length (l) and the base width of the pyramid is (a), the transmittance is integrated through the viewing area and is equal to $T_{total(l)} * a^2/3$. Thus, a linear correlation of a volume versus integrated luminosity plot for a given viewing window should indicate a transmittance proportional to signal intensity (average CCD counts over the viewing area, for example). A flat bottom well with a reflective surface will have a transmittance of $T_{total(2l)}$, and will be about twice as large as $T_{total(l)}$ (when length $<<1^{-cm}$). Thus, the slope of a linear fit of volume versus integrated luminescence intensity for a reflective surface of a given viewing window should be about twice that of a non-reflective surface due to the increased transmittance.

The enzymes suitable for use in the bioluminescent platform reactions of the biosensors are inherently robust and stable, retaining their activity after lyophilization, deposition, and rehydration. The reagent/enzyme mixture or "cocktail" used to detect various metabolites is drawn into the needles after, fabrication, lyophilized (freeze dried) in a stable state, and then packaged for long term storage (up to a year depending on the analytes, reagents, and enzymes needed). The reagent/enzyme mixture includes the ATP and NADH bioluminescent platform enzymes and the enzymes that couple the metabolites to the platforms, as well as all the necessary reagents needed to complete all the reactions that lead to the light output.

The methods used for preparing and storing reagent/enzyme mixtures inside the bioluminescent-based active needle devices are discussed as follows.

1. Drawing of Reagent/Enzyme Mixtures into the Needle Lumen(s)

The reagent enzyme mixtures or "cocktails" are prepared as a "wet" solution in the concentrations needed to detect the desired analytes from the sample volume drawn through the needle lumen. Anti-oxidants and other enzyme stabilizing agents are added to the "cocktail" before lyophilization. These enzyme-stabilizing agents are described below in the lyophilization process.

The prepared wet solutions are drawn into the needles by capillary action. The filling of the needles is ensured by oxidizing the lumen of the needle during the needle fabrication process (or at least using a hydrophilic metal for the lumen of the needle). Each needle lumen has a different "cocktail" for measuring different analytes. Reagents and enzyme-stabilizing agents can be added to an agarose solution which is dried during the lyophilization process and allows for the sample fluid to be drawn into the needle faster by capillary action.

2. Lyophilization Process

Lyophilization stabilizes enzymes for long-term storage by reducing both mechanical and chemical degradation. Appropriate stabilizing excipients and preservatives minimize the denaturation often observed during the processes of lyophilization. Optimized process variables include the initial concentration of enzyme, buffers that exhibit minimal changes in pH with freezing and drying, freezing rate (should be slow), and various additives.

The glass transition temperature of the amorphous phase of the lyophilized enzyme needs to exceed the planned storage temperature of the needle devices. Glass transition temperature of the lyophilized enzyme can be increased by using disaccharides and polymers (used in combination with disaccharides). Disaccharides such as sucrose and trehalose are especially good at stabilizing the enzyme during freezing and dehydration. The sugar to protein weight ratio should be at least about 1 to 1, although stability can be further increased with greater sugar (5 to 1 ratio). Reducing sugars such as glucose, lactose, maltose or maltodextrins should be avoided because of their tendency to degrade proteins through the Maillard reaction between the carbonyls of the sugar and the free amino groups of the protein. Furthermore, surfactants can be used to inhibit aggregation at very low concentrations, such as less that about 0.5% per volume.

Antioxidants such as dithiotheitol and glutathione are used during lyophilization and subsequent storage to prevent oxidation of firefly luciferase due to sulfhydryl groups. Bovine serum albumin can be used for surface passivation. Polyethylene oxide (PEO)-based polymers and surfactants are also effective for surface passivation. Various enzyme preservation and stabilization cocktails are well known and widely used to maintain enzyme activity under dry storage conditions. In one embodiment of the invention, bioluminescent reagents are preserved and stabilized with the following components: (1) 0.45 M glycyl glycine buffer (pH 7.8); (2) 1 mM EDTA; (3) 1 mM dithiothreitol; (4) 10 mM $MgSO_4$; (5) 1 mg/ml of bovine serum albumin; (6) 1 wt % sucrose; and (7) 1 wt % Dextran T-40. It has been found that such a mixture is suitable for stabilization of creatine kinase, a particularly delicate enzyme.

The actual bioluminescent molecules (ATP, FMN, bacterial and firefly luciferase, Oxidoreductase, etc.) are added to the preservative reagents, mixed thoroughly and added to each channel of a pre-chilled biosensor. In one preferred method, the biosensor and reagents are rapidly frozen to about −70° C. followed by a two-stage lyophilization process. The first stage of lyophilization proceeds for 24 hours at about −50° C. and less than about 100 mTorr of pressure. The second stage of lyophilization proceeds for an additional 24 hours at about +30° C. and less than about 100 mTorr of pressure. Air is then re-admitted to the lyophilization chamber and the biosensors are removed. Each completed biosensor is then stored in a black plastic container with a gas tight lid that also contains a desiccant and a humidity indicator membrane. It has been found that this method used with firefly luciferase can preserve more than half the enzymatic bioluminescent activity for a minimum of six months.

The interaction between histidine and $Ni^{++}$ can also be used for immobilization of the enzyme. In biosensor applications, enzymes can be immobilized on a solid support to prevent diffusion (into the sample solution) and minimize interference with other channels of the sensor. The performance of the sensor can be adjusted by changing the immobilized enzyme amount. The recombinant enzymes with BCCP domains can be immobilized through this interaction with high affinity ($Ka=10^{15}M^{-1}$) There are a variety of solid matrices that can be used for immobilization.

Co-immobilization of sequentially operating enzymes improves total reaction efficiency, leading to higher sensitivity. A coupled assay with coimmobilized luciferase and flavin reductase has the advantage that the $FMNH_2$ produced from the flavin reductase can be used more effectively for the luciferase reaction, reducing its autooxidation. Traditional immobilization methods use chemically conjugated enzymes on solid materials, resulting in low immobilization efficiency and low and inconsistent enzyme activity, due to nonspecific immobilization and surface-induced activity loss.

In one, method of the invention, a biotin-avidin system for protein immobilization is utilized, due to its high affinity ($K_a=10^{15}/M$) and stability. In another method, V. harveyi luciferase and FRase I biotinylated is produced in vivo, the proteins are immobilized on avidin-conjugated beads, and the enzyme beads are used to assay NADH. In using this method, it has been found that the co-immobilized enzymes had eight times higher bioluminescence activity than the free enzymes at low enzyme concentration and high NADH concentration. In addition, the immobilized enzymes were more stable than the free enzymes. This immobilization method is also useful to control enzyme orientation, which can increase the efficiency of sequentially operating enzymes like the oxidoreductase-luciferase system.

3. Storage of Active Needle Devices

Storing the bioluminescent-based active needle sensors with the lyophilized "cocktail" in a desiccant will ensure that glass transition temperatures of the lyophilized enzyme are greater than storage temperatures. The active needle devices should be stored in the dark to minimize photooxidation.

Further details regarding bioluminescence-based biosensors as used in the present invention are set forth in the Examples section below.

Figure 10:
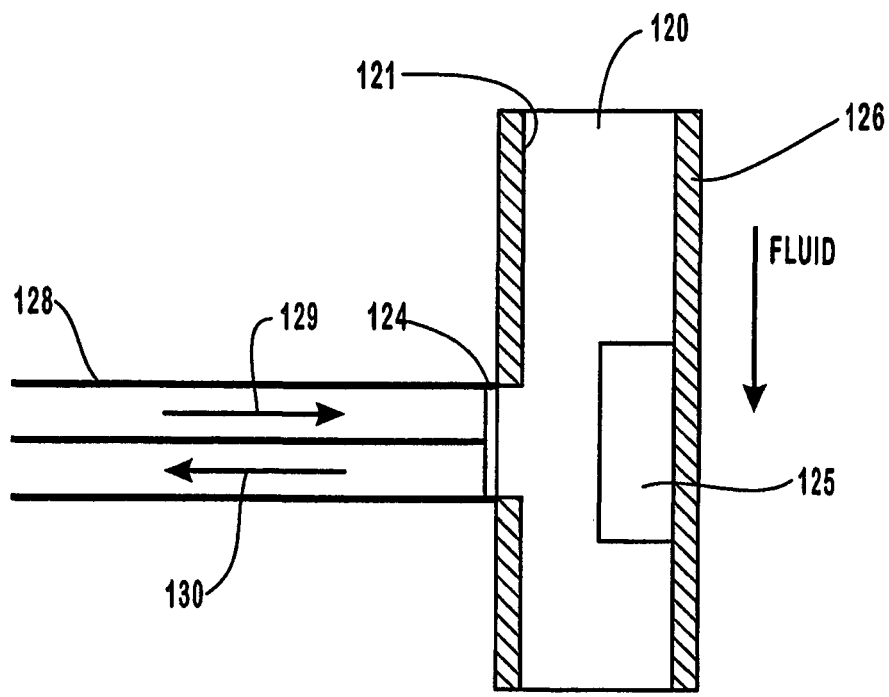
FIG. 10 is a schematic depiction of a pressure sensor in an active microneedle according to the invention.

Another sensor that can be utilized in the needle device of the invention is an integrated pressure sensor in, the form of an optical Fabry-Perot cavity, which is depicted in FIG. 10. The pressure sensor can be integrated into any of the above embodiments by forming a glass plate 120 on one interior surface 121 of a hollow microneedle. A cavity 125 is etched in glass plate 120 on the side of the sensor which is to be in proximity to the fluid flowing in the microchannel of the needle. A thin silicon diaphragm 126 (e.g., about 25 microns thick) is affixed over cavity 125 and is configured to be in direct contact with a fluid whose pressure is to be measured. The diaphragm 126 deflects in response to applied pressure. A light beam 129 (e.g., produced by an LED) is coupled into the sensor through optical fiber 128. The optical fiber 128 optically communicates with the interior of the microneedle through a window 124 in the side of the microneedle. Pressure changes from fluid flowing past diaphragm 126 cause the diaphragm to move. The cavity 125 functions as a Fabry-Perot cavity and the diaphragm reflects varying amounts of light intensity which is directly proportional to the amount of pressure applied to the diaphragm by the fluid. The reflected light can be coupled as a signal out 130 through optical fiber 128 to an appropriate analyzing device for measurement. The change in reflected light can be measured and with proper calibration, can provide a linear measurement of the amount of pressure in the fluid.

The active needle devices of the invention such as the microneedle and microneedle arrays have many benefits and advantages. For fluid injection, these benefits include reduced trauma at penetration sites due to their small size, greater freedom of patient movement because of the minimal penetration depth of the needles, a practically pain-free drug delivery due to the smaller cross section of the needle tip and distribution of fluid force, and precise control of penetration depth from needle extension length. In addition, the microneedles have the ability to deliver drugs to localized areas, or extract fluids from precise locations for analysis, and are advantageous in their ability to be stacked and packaged into a three-dimensional device for fluid transfer. The active microneedles have the ability to extract either large or small amounts of fluids in precisely controlled amounts, and can be easily and economically fabricated using micromachining procedures.

The active microneedles also provide convenient and easy methods for performing electrical, optical, physical, or biochemical sensing in compact devices. The integrated sensing capabilities in the active microneedles provide compact, portable, and disposable devices which are less costly and complex to use for analysis of fluid samples, and reduce or eliminate the need for supporting fluidic and electronic systems.

The microneedles can be used in a wide variety of biomedical applications. The microneedles can withstand typical handling and can subcutaneously deliver medication without the usual discomfort associated with conventional needles. The microneedles are minimally invasive, in that the microneedles only penetrate just beyond the viable epidermis, reaching the capillaries and minimizing the chance of encountering and damaging the nerves present in the area of penetration.

The following examples are given to illustrate the present invention, and are not intended to limit the scope of the invention.

EXAMPLE 1

A two dimensional microneedle array was fabricated with 25 hollow microneedles fluidly interconnected by a needle coupling channel. The hollow microneedles were made such that their inner cross-sectional area was $40 \times 20\ \mu m^2$ (width by height) and their outer cross-sectional area was $80 \times 60\ \mu m^2$. The needle coupling channel was 100 µm wide, and provided fluid communication between each needle channel. Two sets of $60 \times 100\ \mu m^2$ structural supports were located 250 µm from each needle end. Each needle channel was 2 mm long, while the width of the 25 needle array was 5.2 mm. The center-to-center spacing between individual needles was 200 µm. The needle walls were made of electroformed metal and were approximately 20 µm thick.

The microneedle array was fabricated from electroformed low stress nickel sulphamate, gold cyanide, and palladium electroforming solutions. The bath chemistry and electroplating conditions were selected and precisely controlled to allow formation of low stress depositions on top of a 3-5 µm sacrificial membrane. The surface roughness of the electroplated metals was found by Atomic Force Microscope (AFM) to be approximately 15 nm, resulting in a relative roughness of 0.00056.

It is important to note the structural quality of the needle tips. The inner dimensions were approximately $30 \times 20\ \mu m^2$, outer dimensions were approximately 80×60 μm², and the needle tips were formed with 45° angles for ease of penetration.

EXAMPLE 2

Individual hollow metallic microneedles were fabricated with multiple output ports and had an inner cross-sectional area of 140×21 μm² (width by height) with outer cross-sectional area dimensions of 200×60 μm². The tip dimensions of the microneedles were less than 15×15 μm². The length of the tapered portion of the needle shaft was 1 mm and the distance from the tip to the first output port was about 300 μm. The total length of each microneedle was 6 mm, with input port inner dimensions of 140 μm wide and 21 μm high. The wall thickness of each microneedle was about 20 μm, and the output ports were formed with dimensions of 30 μm² on the top and bottom of the microneedles. The output ports were separated by 30 μm, and there were 9 ports on the top and 12 ports on the bottom of each microneedle.

The microneedles were each packaged into a standard Luer-lock fitting using a polymeric medical grade UV-curable adhesive. This interface between a microneedle and a syringe included a simple female Luer-to-1/16" barb adapter. The UV-curable adhesive was found to permanently affix the microneedle to the interface while providing a leak resistant seal.

EXAMPLE 3

Figure 11:
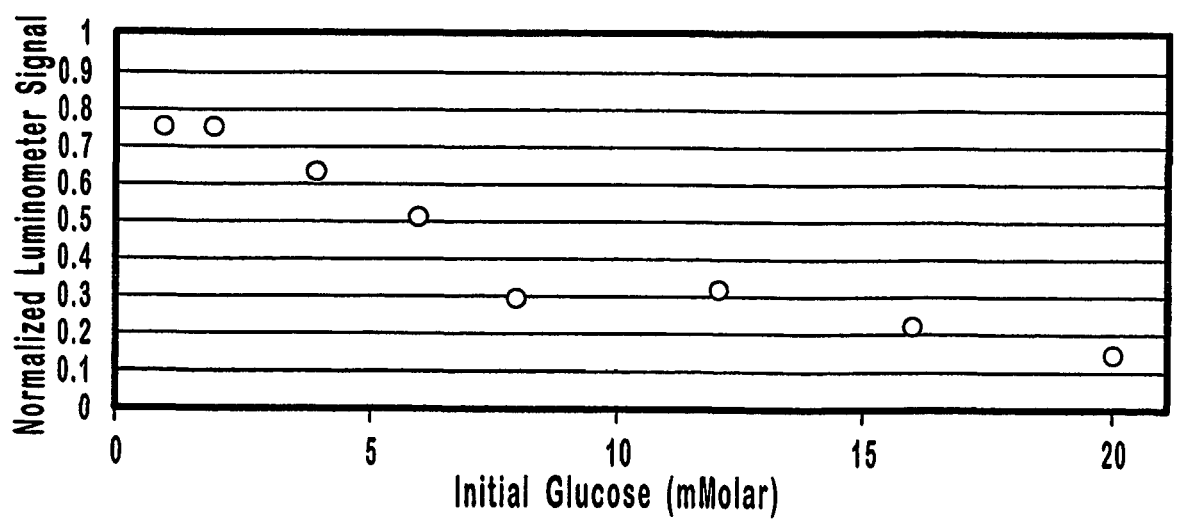
FIG. 11 is a graph of the normalized bioluminescent signal as a function of glucose concentration.

A preliminary experiment was conducted to assay a glucose via glucokinase and firefly luciferase reactions. The assay was a homogeneous ATP depletion type assay with initial concentrations of glucokinase (80 nano-molar), ATP (10 micro-molar), luciferin (100 micro-molar), and firefly luciferase (0.1 nano-molar) in 0.45 M glycyl glycine buffer at pH 7.8. The results are shown in the graph of FIG. 11, which plots the normalized luminometer bioluminescence, detected two minutes after the rapid mixing of all reactants, as a function of initial glucose concentration. The results suggest that a single step homogeneous assay for glucose can be accomplished without initial dilution of the glucose in the sample.

EXAMPLE 4

Figure 12:
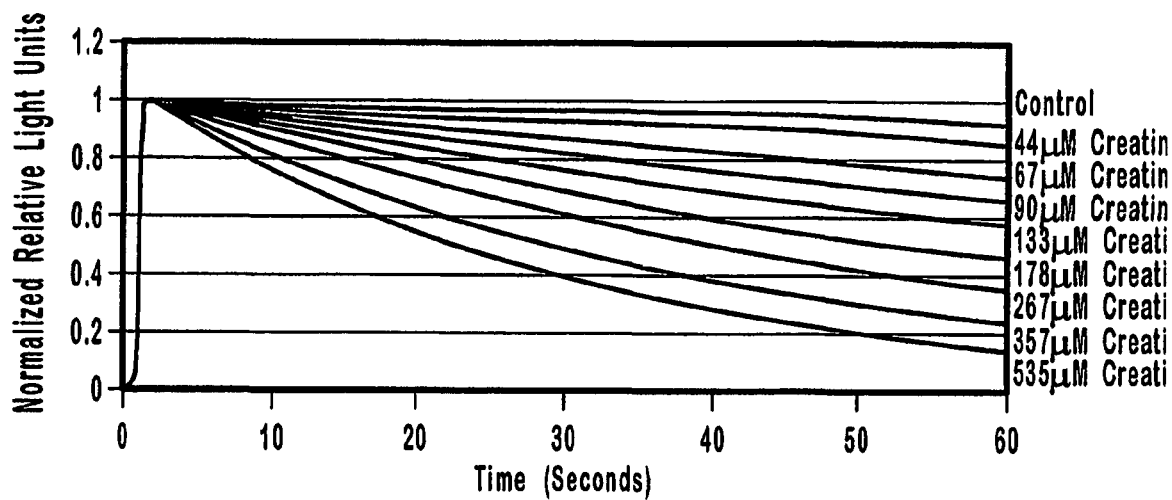
FIG. 12 is a graph of the normalized bioluminescent signal as a function of time for several different concentrations of creatine.
Figure 13:
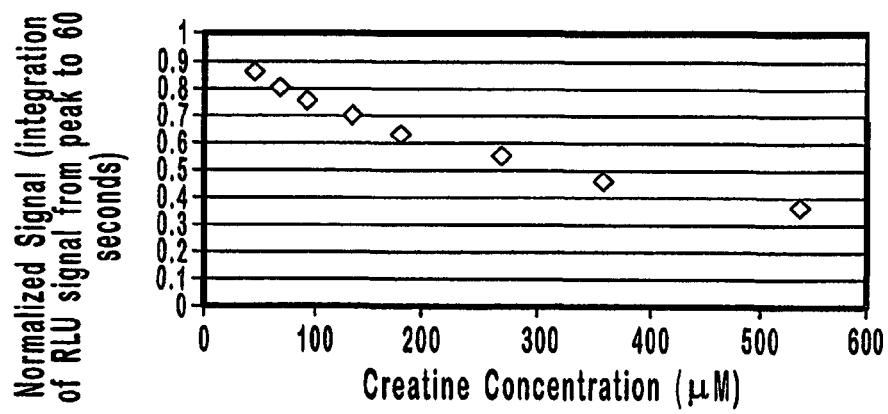
FIG. 13 is a graph of the normalized bioluminescent signal as a function of creatine concentration.

FIGS. 12 and 13 are graphs showing the characteristics for a creatine biosensor. The graph of FIG. 12 plots the normalized bioluminescent signal (in relative light units) as a function of time for several different concentrations of creatine. The bioluminescent signal had a 560 nm wavelength and was measured by a luminometer. The final concentrations of creatine shown are within the physiological serum creatine concentration range.

FIG. 13 shows the results of an assay experiment for creatine using the creatine kinase and firefly luciferase reactions. The creatine assay was a homogeneous ATP depletion assay (the creatine kinase reaction competes with the firefly luciferase reaction for the ATP). The final assay constituents were buffered in 0.45 molar glycine-glycine buffer at pH 7.8 and the final assay concentrations were the following: 1.4 μM ATP, 71 μM $Mg^{2+}$, 14 μM luciferin, 0.3 μM luciferase, 60 μM creatine kinase, and various concentrations of creatine (0.45 M glycine-glycine buffer for control). Relative light units (RLU) measured by the luminometer are dependent on the type of instrument, sensitivity of the instrument, and other factors; therefore, the raw bioluminescence signal measured versus time was normalized to the control peak RLU value. FIG. 13 plots the normalized bioluminescent signal as a function of creatine concentration.

EXAMPLE 5

In order to determine the feasibility and the physical limitations of using bioluminescence for highly sensitive analyte measurement of small sample volumes, micro-reaction chambers (μRCs) were fabricated on silicon wafers using KOH anisotropic wet etching. An ATP firefly luciferase/luciferin solution was placed in the μRCs and observed through a close up lens with a CCD. The integrated CCD signal was recorded and compared with well size and depth. The attenuation of the CCD signal was also observed for wafers coated with titanium (500 Å) followed by chromium (1500 Å).

A 5-mL firefly luciferase/luciferin solution consisted of 1.25 mg/mL bovine serum albumin (Sigma—reconstituted into the solution and used for coating the glass vial to prevent denaturing of the luciferase), 1.25 mM ethylene diaminetetra acetic acid (Sigma), 12.5 mM $Mg^{++}$ (Sigma—from $MgSO_4$), 1.84-μM firefly luciferase (Promega), and 1.25 mM luciferin (Biosynth) in a 1.25 mM glycyl-glycine buffer. This mixture was able to maintain 90% activity for about 20 hours when stored in the dark. A 5 mM ATP, glycyl-glycine buffer solution was also prepared. A 20 μL sample of the firefly luciferase/luciferin solution was pipetted into 5 μL of the ATP solution that resulted in a 1.0 mM ATP mixture, saturated with luciferase and luciferin (which means the reaction rate was at its peak). After the solution mixed, 20 μL of it was pipetted onto an area about 20×15 mm wide. A thin glass cover slip was placed on the solution, starting at one end and tilting the cover slip as it was laid down, so that the excess bioluminescent fluid would disperse. For high concentrations of ATP (>8 μM), the initial mixing of ATP with the luciferase/luciferin solution causes a peak luminescence within 3 seconds. The luminescence then tapers and levels off after 1 minute. Therefore, the light measurements for this experiment were integrated for 20 seconds, 2 minutes after the ATP and luciferase/luciferin solution were mixed, with the light intensity essentially constant.

An ST6-A CCD camera, from Santa Barbara Instruments Group was fitted with an Olympus wide-angle lens and close-up ring. The experimental substrates were focused 55 mm below the lens with the aperture set at 2.8. The field of view was about 20×15 mm. The camera was operated at −20.00 ° C. One minute after the luciferase/luciferin solution was, added to the ATP, a 10-sec dark field exposure was taken with the CCD. At 2 minutes and 5 seconds after the ATP and luciferase/luciferin solution mixed, the CCD integrated a 20 second exposure, of the bioluminescent reaction while shrouded in a darkroom. The resulting image was saved as a TIF file (Range: 0-400). Scion Image (based on the NIH image software) was used to determine the average and standard deviation of the pixel values for each μRC. One pixel of the CCD image was equal to 46.875 μm. Actual results failed to show light emitting from the 75, 50, 25, and 10 μm wide wells on all substrates.

Figure 14:
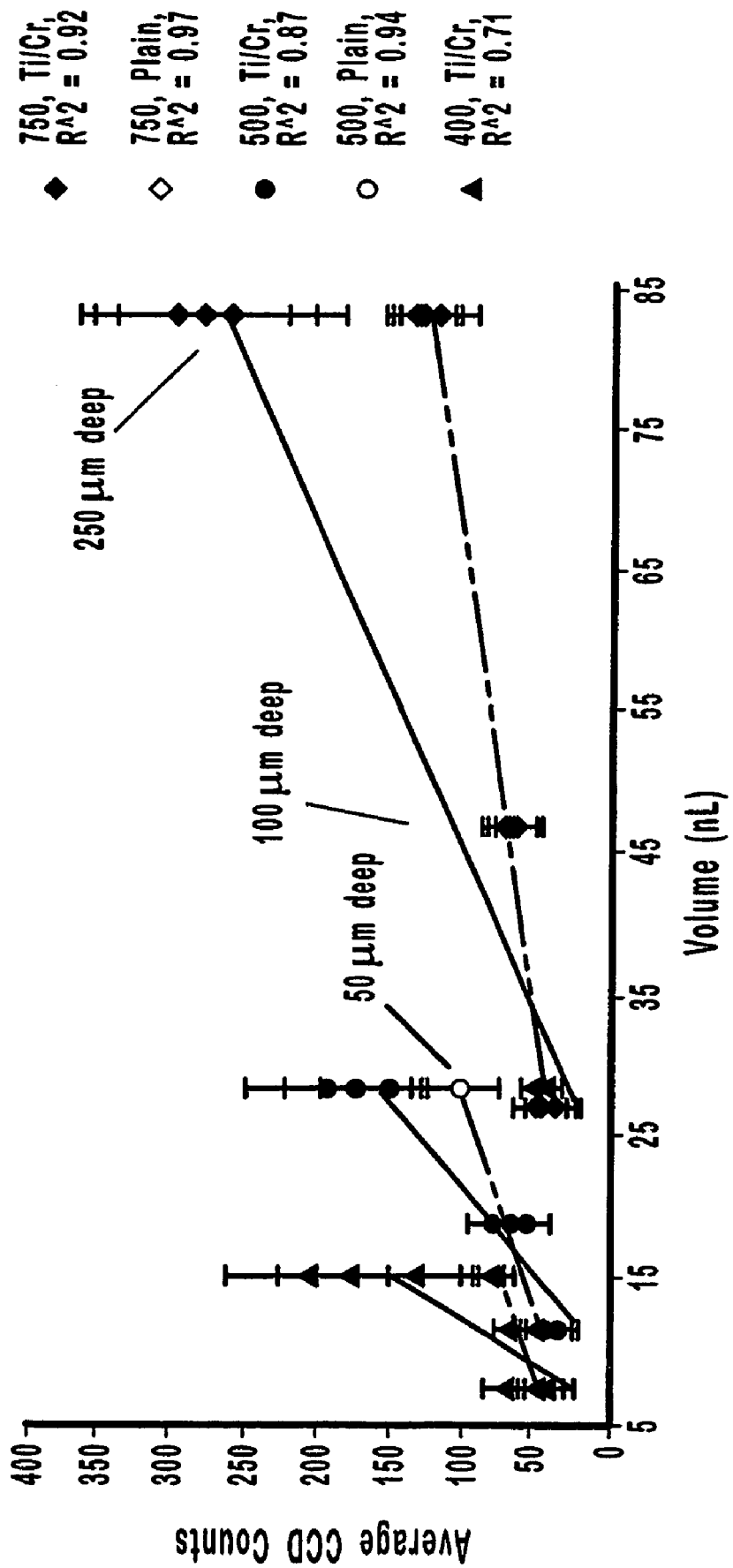
FIG. 14 is a graph of the average CCD counts as a function of volume for different sample volumes.

FIG. 14 is a graph of the average CCD counts from the 20 second integrated CCD reading as a function of different sample volumes. The data was plotted in sets for the same viewing area (or μRC square width). The data was also separated according to Ti/Cr reflective substrates and plain, non-reflective substrates. For each set of data (wells with same width and coating), the increasing volume occurs from the increased etch depths of 250 μm 100 μm, and 50 μm. The data from the different etch depths are pointed out for the 750 μm wide wells as an example. The higher intensity values occurred for the deeper wells. The intensity/volumes slope is greater for the Ti/Cr reflective substrates than for the plain substrates.

Table 1 below sets forth a statistical comparison of the intensity/volume slope relationships for reflective vs. non-reflective surfaces of the same viewing window size. The reflective wells with intensity/volume slopes that were statistically different from the intensity/volume slopes for the non-reflective surfaces (P<0.05 using the T-test) were over two times greater. This follows the hypothesis that transmittance is nearly doubled for chromium coated (reflectivity=0.67@560 nm) versus uncoated silicon (reflectivity=0.33 @ 560 nm) µRCs.

The T-test used was the student-T test to find if there was a significant difference between sample measurements of two groups. The null hypothesis of the T-test (for the described experiment of this example) was: there is no difference in the intensity/volume slopes for the wells with reflective surfaces and the wells with non-reflective surfaces. The value P<0.05 means that there is less than a 5% probability (P) that the null hypothesis is true. The T-test, if performed properly, is a useful tool to show that one method or product is significantly different (more efficient, better, etc.) than an existing method or product.

TABLE 1

| µRC Width (µm) | P value from T-test between Intensity/Volume Slopes of Non-Reflective µRCs and Reflective µRCs | Ratio of Intensity/Volume Slopes for Reflective and Non-Reflective Substrates |
| --- | --- | --- |
| 750 | 0.00001 | 3.02 |
| 500 | 0.002 | 2.37 |
| 400 | 0.004 | 4.94 |
| 300 | 0.005 | 5.11 |
| 250 | 0.36 | 2.87 |
| 200 | 0.030 | 1.07 |
| 150 | 0.72 | 0.88 |
| 100 | 0.55 | 0.21 |

The intensity/volume slope also increases as the µRC square width decreases. This implies that using long, narrow microneedles as the µRC is ideal. Table 2 statistically compares the intensity/volume slopes between reflective wells of different viewing window sizes, showing that there is a significant increase in the intensity/volumes slopes, as the µRC width decreases. The intensity/volume slope ratio is the slope for the smaller window over the slope for the next larger window.

TABLE 2

| µRC Square Widths Being Compared (µm) | P value from T-test between Intensity/Volume Slopes µRCs being compared | Ratio of Intensity/Volume Slopes for Smaller µRC Widths Verses Wider µRC Widths |
| --- | --- | --- |
| 500/750 | 0.004 | 1.89 |
| 400/500 | 0.04 | 1.98 |
| 300/400 | 0.28 | 1.59 |
| 250/300 | 0.89 | 1.11 |
| 200/250 | 0.81 | 1.28 |
| 150/200 | 0.91 | 0.73 |

The increase in intensity/volume is only significant down to wells that are 400 µm wide. For smaller µRC widths (150-300 µm), the non-reflective substrates show little correlation between average CCD counts and sample volumes ($R^2$<0.25, where R is the reflectivity). The Ti/Cr reflective substrates still show some correlation ($R^2$>0.25 for µRCs 250 µm wide and wider) between intensity and volume. However, as the µRC square width decreases (250 µm wide and smaller), there is little difference in signal intensity values for different etch depths. The error in the signals for wells 200 µm wide and smaller is large enough to overlap with the background intensity. This suggests that the wells with windows smaller than 200 µm wide would not produce signals of a discernable intensity, if they are only 250 µm deep. However, narrower and deeper µRCs such as microneedles, which hold a larger sample volume, would produce a stronger useable signal.

The present invention may be embodied in other specific forms without, departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An active microneedle device comprising:
   a hollow microneedle having an elongated shaft defining at least one microchannel and having a proximal and distal end;
   at least one input port at said proximal end of said elongated shaft and at least one output port at said distal end of said elongated shaft, said at least one microchannel providing fluid communication between said at least one input port and said at least one output port; and
   at least one non-living bioluminescence-based biosensor located in said elongated shaft, said at least one non-living bioluminescence-based biosensor including a reagent mixture, said reagent mixture including one or more anti-oxidant additives adapted to reduce oxidation due to sulfhydryl groups in the reagent mixture, and said reagent mixture further being stabilized for long-term storage such that at least half of its bioluminescent activity is preserved for at least six months,
   wherein said elongated shaft is formed of a first material and has an interior surface which has a coating formed of a second material, wherein said second material is a light enhancing reflective coating relative to said first material.

2. The active microneedle device of claim 1, wherein said non-living bioluminescence-based biosensor includes a stabilized luciferase enzyme and a stabilized luciferin substrate.

3. The active microneedle device of claim 1, wherein said non-living bioluminescence-based biosensor is lyophilized.

4. The active microneedle device of claim 1, wherein said at least one non-living bioluminescence-based biosensor is located at said output port of said elongated shaft.

5. The active microneedle device of claim 1, wherein said bioluminescence-based biosensor is over a range of five or more orders of magnitude of concentration ranges.

6. The active microneedle device of claim 1, further comprising an optical detector adapted to detect light transmittance levels generated by a reaction of said at least one non-living bioluminescence-based biosensor with a fluid within said microchannel.

7. The active microneedle device of claim 6, wherein said optical detector is integrated inside said hollow microneedle.

8. The active microneedle device of claim 6, wherein said optical detector is external to said hollow microneedle.

9. The active microneedle device of claim 8, wherein said elongate shaft has a window therein, and wherein said external optical detector detects said light transmittance levels through said window.

10. The active microneedle device of claim 1, wherein said at least one non-living bioluminescence-based biosensor is adapted to detect light transmittance levels of a sample size less than or about equal to 0.05 μL.

11. The active microneedle device of claim 1, wherein said microchannel has a pyramid-shaped cross section along its elongate length.

12. The active microneedle device of claim 3, wherein said at least one non-living bioluminescence-based biosensor comprises a biochemical sensing reagent mixture configured to complete a reaction leading to light generation, and wherein said biochemical sensing reagent mixture has been stabilized by drawing said biochemical sensing reagent mixture into said elongated shaft, and thereafter lyophilizing said biochemical sensing reagent.

13. The active microneedle device of claim 12, wherein said biochemical sensing reagent mixture includes ATP and NADH bioluminescent platform enzymes.

14. The active microneedle device of claim 12, wherein said one or more anti-oxidants substantially prevent oxidation of luciferase due to sulfhydryl groups.

15. The active microneedle device of claim 12, wherein said biochemical sensing reagent mixture includes an agarose solution.

16. The active microneedle device of claim 12, wherein said biochemical sensing reagent mixture inside said elongated shaft includes sucrose or trehalose.

17. The active microneedle device of claim 12, wherein said at least one non-living bioluminescence-based biosensor comprises one or more bioluminescent molecules, and wherein said one or more bioluminescent molecules have been stabilized within said elongated shaft.

18. The active microneedle device of claim 12, wherein said non-living bioluminescence-based biosensor includes one or more operating enzymes, and wherein said one or more operating enzymes have been immobilized.

19. The active microneedle device of claim 18, wherein said one or more operating enzymes includes at least two sequentially operating enzymes that have been co-immobilized, said at least two sequentially operating enzymes having been mixed together prior to introduction into said microchannel.

20. The active microneedle device of claim 1, wherein said elongated shaft of said hollow microneedle is a non-silicon material.

21. The active microneedle device of claim 1, wherein said at least one microchannel has a cross-sectional area in a range from about 25 μm² to about 5000 μm².

22. The active microneedle device of claim 1, wherein said elongated shaft of said hollow microneedle is composed of a metal material selected from a group consisting of: nickel, copper, gold, silver, platinum, palladium, titanium, chromium, and alloys or combinations thereof.

23. The active microneedle device of claim 1, wherein said elongated shaft is supported on a substrate, said substrate having a substantially planar surface and an edge adjacent said substantially planar first surface.

24. An active needle device comprising:
a hollow needle having an elongated shaft defining at least one channel and having a proximal and distal end;
at least one input port at said proximal end of said elongated shaft and at least one output port at said distal end of said elongated shaft, said at least one channel providing fluid communication between said at least one input port and said at least one output port; and
at least one non-living bioluminescence-based biosensor located in said elongated shaft, said at least one non-living bioluminescence-based biosensor including a reagent mixture, said reagent mixture including one or more anti-oxidant additives, and said reagent mixture further being stabilized for long-term storage such that at least half of its bioluminescent activity is preserved for at least six months,
wherein said elongated shaft is formed of a first material and has an interior surface which has a coating formed of a second material, wherein said second material is a light enhancing reflective coating relative to said first material.

25. The active needle device of claim 24, wherein said hollow needle is a macroneedle.

26. A biosensor comprising:
(i) a hollow microneedle, said hollow microneedle including:
(a) a tapered tip at a distal end of said hollow microneedle;
(b) an output port proximate said tapered tip;
(c) an input port at a proximal end of said hollow microneedle;
(d) an elongate channel disposed between said input port and said tapered tip, said elongate channel having an interior surface that is formed of said first material, and said elongate channel providing fluid communication between said input port and said output port, wherein said elongate channel has a substantially constant cross-section across its entire elongate length between said input port and said tapered tip; and
(e) a light enhancing reflective coating deposited on said first material of said interior surface of said elongate channel, said light enhancing reflective coating providing for light transmittance levels about twice that of said first material;
(ii) a non-living bioluminescence-based biosensor deposited on said interior surface of said elongate channel, said non-living bioluminescence-based biosensor being dried on said interior surface and including a variety of components that were thoroughly mixed as a wet solution for depositing said non-living bioluminescence-based biosensor in a wet form on said interior surface prior to drying, said variety of components including at least:
(a) bioluminescent molecules;
(b) anti-oxidant additives for reducing oxidation of said bioluminescent molecules due to sulfhydryl groups and for surface passivation; and
(d) one or more stabilizer additives adapted to stabilize enzymes of said bioluminescent molecules; and
(iii) an optical detector configured to detect luminescence intensity levels within said elongate channel, said optical detector being integrated within said interior surface of said elongate channel.

27. The biosensor of claim 26, wherein said variety of components further include an agarose solution configured to facilitate rapid drawing of said wet solution into said elongate channel.

28. The biosensor of claim 26, wherein said one or more stabilizer additives are configured to co-immobilize sequentially operating enzymes of said bioluminescent molecules.

29. The biosensor of claim 28, wherein said one or more stabilizer additives include avidin and are adapted to immobilize proteins.

30. The biosensor of claim 28, wherein said one or more stabilizer additives are adapted to control enzyme orientation.

31. The biosensor of claim 30, wherein said enzyme orientation increases efficiency of sequentially operating enzymes.

32. The biosensor of claim 26, wherein said elongate channel was oxidized during fabrication or is formed of a hydrophilic metal.

* * * * *

UNITED STATES PATENT AND TRADEMARK OFFICE
CERTIFICATE OF CORRECTION

PATENT NO. : 7,473,244 B2
APPLICATION NO. : 10/258011
DATED : January 6, 2009
INVENTOR(S) : Frazier et al.

It is certified that error appears in the above-identified patent and that said Letters Patent is hereby corrected as shown below:

Column 1
Line 29, after "purposes" and before "or" omit ","
Line 32, after "which" add --are on the order of millimeters (mm) and--
Line 33, after "cell" omit "and are on the order of millimeters (mm)"
Line 35, change ";" to --:--
Line 36, after "location" and before "or" omit ","

Column 2
Line 43, after "equalization" and before "and" omit ","

Column 3
Line 34, after "particular" and before "description" omit ","

Column 4
Line 63, after "thereof" and before "For" insert --.--

Column 6
Line 43, after "devices" and before "as" insert --,--

Column 7
Line 13, change "structural" to --Structural--
Line 47, after "bottom walls," omit "aside walls" and insert --side walls, or top walls--
Line 66, after "devices" and before "as" insert --,--

Column 8
Line 60, after "arrays" and before "such" insert --,--

Column 10
Line 55, change "BIOLUESCENT" to --BIOLUMINESCENT--

Column 11
Line 17, after "configuration" and before "is" omit ",". Also, change "then" to --,then,--

Column 12
Line 26, change "since" to --Since--

Column 13
Line 22, before "Assuming" insert --Also--. Also, change "Assuming" to --assuming--

UNITED STATES PATENT AND TRADEMARK OFFICE
CERTIFICATE OF CORRECTION

PATENT NO. : 7,473,244 B2
APPLICATION NO. : 10/258011
DATED : January 6, 2009
INVENTOR(S) : Frazier et al.

It is certified that error appears in the above-identified patent and that said Letters Patent is hereby corrected as shown below:

Column 15
Line 9, after "$(Ka=10^{15}M^{-1})$" insert --.--
Line 14, change "that" to --of--
Line 15, after "reductase" insert --, which--
Line 21, after "one" and before "method" omit ","

Column 17
Line 36, change "glycyl glycine" to --glycyl-glycine--

Column 18
Line 51, after "exposure" and before "of" omit ","

Column 19
Line 15, change "student-T test" to --student T-test--

Column 20
Line 14, after "without" and before "departing" omit ","

Column 21
Line 2, change "elongate" to --elongated--
Line 11, change "elongate" to --elongated--

Signed and Sealed this

Twenty-sixth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,473,244 B2  Page 1 of 1
APPLICATION NO. : 10/258011
DATED : January 6, 2009
INVENTOR(S) : Frazier et al.

It is certified that error appears in the above-identified patent and that said Letters Patent is hereby corrected as shown below:

Title Page, insert
-- (60) Related U.S. Application Data
Provisional application No. 60/208,868, filed on 06/02/2000 --.

Signed and Sealed this

Twentieth Day of July, 2010

David J. Kappos
*Director of the United States Patent and Trademark Office*